US012582800B2

(12) United States Patent
Desrosiers

(10) Patent No.: US 12,582,800 B2
(45) Date of Patent: Mar. 24, 2026

(54) TRANSCATHETER DELIVERY APPARATUS

(71) Applicant: EDWARDS LIFESCIENCES CORPORATION, Irvine, CA (US)

(72) Inventor: John J. Desrosiers, San Clemente, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 396 days.

(21) Appl. No.: 18/315,498

(22) Filed: May 11, 2023

(65) Prior Publication Data

US 2023/0277809 A1     Sep. 7, 2023

Related U.S. Application Data

(63) Continuation of application No. PCT/US2021/058723, filed on Nov. 10, 2021.

(60) Provisional application No. 63/112,326, filed on Nov. 11, 2020.

(51) Int. Cl.
*A61M 25/01*     (2006.01)
*A61M 25/00*     (2006.01)
*A61M 25/09*     (2006.01)

(52) U.S. Cl.
CPC ........ *A61M 25/01* (2013.01); *A61M 25/0069* (2013.01); *A61M 2025/09183* (2013.01)

(58) Field of Classification Search
CPC .......................... A61M 25/01; A61M 25/0069
See application file for complete search history.

(56) References Cited

U.S. PATENT DOCUMENTS

| | | | |
|---|---|---|---|
| 519,297 | A | 5/1894 | Bauer |
| 4,035,849 | A | 7/1977 | Angell et al. |
| 4,592,340 | A | 6/1986 | Boyles |
| 4,955,895 | A | 9/1990 | Sugiyama et al. |
| 4,994,077 | A | 2/1991 | Dobben |
| 5,059,177 | A | 10/1991 | Towne et al. |
| 5,176,698 | A | 1/1993 | Burns et al. |
| 5,192,297 | A | 3/1993 | Hull |
| 5,266,073 | A | 11/1993 | Wall |
| 5,325,845 | A | 7/1994 | Adair |
| 5,358,496 | A | 10/1994 | Ortiz et al. |
| 5,411,552 | A | 5/1995 | Andersen et al. |
| 5,554,185 | A | 9/1996 | Block et al. |
| 5,591,195 | A | 1/1997 | Taheri et al. |

(Continued)

FOREIGN PATENT DOCUMENTS

| | | |
|---|---|---|
| DE | 19532846 A1 | 3/1997 |
| DE | 19907646 A1 | 8/2000 |

(Continued)

*Primary Examiner* — Daniel L Cerioni
(74) *Attorney, Agent, or Firm* — Klarquist Sparkman LLP

(57)     ABSTRACT

Embodiments of a nosecone for a transcatheter delivery apparatus are disclosed. The nosecone can include a distal portion and a proximal portion. A longitudinal axis can extend from a distal end of the distal portion to a proximal end of the proximal portion. The proximal portion can have a shoulder region adjacent the distal portion of the nosecone and a body region proximal to the shoulder region. An outer surface of the nosecone can have a cross-sectional profile taken along the longitudinal axis of the nosecone. The cross-sectional profile of the body region can have a convex shape when viewed from a centroid of the body region.

9 Claims, 7 Drawing Sheets

(56) References Cited

U.S. PATENT DOCUMENTS

| | | | |
|---|---|---|---|
| 5,599,305 A | 2/1997 | Hermann et al. | |
| 5,632,760 A | 5/1997 | Sheiban et al. | |
| 5,639,274 A | 6/1997 | Fischell et al. | |
| 5,728,068 A | 3/1998 | Leone et al. | |
| 5,749,890 A | 5/1998 | Shaknovich | |
| 5,782,809 A | 7/1998 | Umeno et al. | |
| 5,824,044 A | 10/1998 | Quiachon et al. | |
| 5,840,081 A | 11/1998 | Andersen et al. | |
| 5,908,405 A | 6/1999 | Imran et al. | |
| 5,916,147 A | 6/1999 | Boury | |
| 5,944,690 A | 8/1999 | Falwell et al. | |
| 5,961,536 A | 10/1999 | Mickley et al. | |
| 5,968,068 A | 10/1999 | Dehdashtian et al. | |
| 6,019,777 A | 2/2000 | Mackenzie | |
| 6,027,510 A | 2/2000 | Alt | |
| 6,033,381 A | 3/2000 | Kontos | |
| 6,143,016 A | 11/2000 | Bleam et al. | |
| 6,162,208 A | 12/2000 | Hipps | |
| 6,168,614 B1 | 1/2001 | Andersen et al. | |
| 6,174,327 B1 | 1/2001 | Mertens et al. | |
| 6,217,585 B1 | 4/2001 | Houser et al. | |
| 6,235,050 B1 | 5/2001 | Quiachon et al. | |
| 6,251,092 B1 | 6/2001 | Qin et al. | |
| 6,379,372 B1 | 4/2002 | Dehdashtian et al. | |
| 6,383,171 B1 | 5/2002 | Gifford et al. | |
| 6,454,799 B1 | 9/2002 | Schreck | |
| 6,458,153 B1 | 10/2002 | Bailey et al. | |
| 6,461,382 B1 | 10/2002 | Cao | |
| 6,471,672 B1 | 10/2002 | Brown et al. | |
| 6,500,147 B2 | 12/2002 | Omaleki et al. | |
| 6,514,228 B1 | 2/2003 | Hamilton et al. | |
| 6,527,979 B2 | 3/2003 | Constantz et al. | |
| 6,579,305 B1 | 6/2003 | Lashinski | |
| 6,582,462 B1 | 6/2003 | Andersen et al. | |
| 6,652,578 B2 | 11/2003 | Balley et al. | |
| 6,730,118 B2 | 5/2004 | Spenser et al. | |
| 6,733,525 B2 | 5/2004 | Yang et al. | |
| 6,764,504 B2 | 7/2004 | Wang et al. | |
| 6,767,362 B2 | 7/2004 | Schreck | |
| 6,830,584 B1 | 12/2004 | Seguin | |
| 6,893,460 B2 | 5/2005 | Spenser et al. | |
| 6,908,481 B2 | 6/2005 | Cribier | |
| 7,011,094 B2 | 3/2006 | Rapacki et al. | |
| 7,018,406 B2 | 3/2006 | Seguin et al. | |
| 7,018,408 B2 | 3/2006 | Bailey et al. | |
| 7,137,993 B2 | 11/2006 | Acosta et al. | |
| 7,276,084 B2 | 10/2007 | Yang et al. | |
| 7,318,278 B2 | 1/2008 | Zhang et al. | |
| 7,320,702 B2 | 1/2008 | Hammersmark et al. | |
| 7,320,704 B2 | 1/2008 | Lashinski et al. | |
| 7,374,571 B2 | 5/2008 | Pease et al. | |
| 7,393,360 B2 | 7/2008 | Spenser et al. | |
| 7,435,257 B2 | 10/2008 | Lashinski et al. | |
| 7,510,575 B2 | 3/2009 | Spenser et al. | |
| 7,585,321 B2 | 9/2009 | Cribier | |
| 7,594,926 B2 | 9/2009 | Linder et al. | |
| 7,597,709 B2 | 10/2009 | Goodin | |
| 7,618,446 B2 | 11/2009 | Andersen et al. | |
| 7,780,723 B2 | 8/2010 | Taylor | |
| 7,785,366 B2 | 8/2010 | Maurer et al. | |
| 7,942,924 B1 * | 5/2011 | Perez | A61F 2/966 |
| | | | 623/1.23 |
| 7,959,661 B2 | 6/2011 | Hijlkema et al. | |
| 8,029,556 B2 | 10/2011 | Rowe | |
| 8,167,932 B2 | 5/2012 | Bourang et al. | |
| RE43,882 E | 12/2012 | Hopkins et al. | |
| 8,449,606 B2 | 5/2013 | Ellasen et al. | |
| 8,475,523 B2 | 7/2013 | Duffy | |
| 8,568,472 B2 | 10/2013 | Marchand et al. | |
| 9,061,119 B2 | 6/2015 | Le et al. | |
| 9,119,716 B2 | 9/2015 | Lee et al. | |
| 9,795,477 B2 | 10/2017 | Tran et al. | |
| 11,273,038 B2 | 3/2022 | Tang et al. | |
| 2001/0002445 A1 | 5/2001 | Vesely | |
| 2001/0007082 A1 | 7/2001 | Dusbabek et al. | |

| | | | |
|---|---|---|---|
| 2002/0032481 A1 | 3/2002 | Gabbay | |
| 2002/0058995 A1 | 5/2002 | Stevens | |
| 2002/0165461 A1 | 11/2002 | Hayzelden et al. | |
| 2003/0040792 A1 | 2/2003 | Gabbay | |
| 2003/0050694 A1 | 3/2003 | Yang et al. | |
| 2003/0120341 A1 | 6/2003 | Shennib et al. | |
| 2004/0093061 A1 | 5/2004 | Acosta et al. | |
| 2004/0133263 A1 | 7/2004 | Dusbabek et al. | |
| 2004/0143197 A1 | 7/2004 | Soukup et al. | |
| 2004/0186563 A1 | 9/2004 | Lobbi | |
| 2004/0186565 A1 | 9/2004 | Schreck | |
| 2004/0260389 A1 | 12/2004 | Case et al. | |
| 2005/0080474 A1 | 4/2005 | Andreas et al. | |
| 2005/0096736 A1 | 5/2005 | Osse et al. | |
| 2005/0137689 A1 | 6/2005 | Salahieh et al. | |
| 2005/0149160 A1 | 7/2005 | McFerran | |
| 2005/0203614 A1 | 9/2005 | Forster et al. | |
| 2005/0203617 A1 | 9/2005 | Forster et al. | |
| 2005/0245894 A1 | 11/2005 | Zadno-Azizi | |
| 2006/0025857 A1 | 2/2006 | Bergheim et al. | |
| 2006/0282150 A1 | 12/2006 | Olson et al. | |
| 2007/0005131 A1 | 1/2007 | Taylor | |
| 2007/0073389 A1 | 3/2007 | Bolduc et al. | |
| 2007/0088431 A1 | 4/2007 | Bourang et al. | |
| 2007/0100356 A1 | 5/2007 | Lucatero et al. | |
| 2007/0112422 A1 | 5/2007 | Dehdashtian | |
| 2007/0203575 A1 | 8/2007 | Forster et al. | |
| 2007/0219612 A1 | 9/2007 | Andreas et al. | |
| 2007/0239254 A1 | 10/2007 | Chia et al. | |
| 2007/0244546 A1 | 10/2007 | Francis | |
| 2007/0265700 A1 | 11/2007 | Eliasen et al. | |
| 2008/0065011 A1 | 3/2008 | Marchand et al. | |
| 2008/0103520 A1 | 5/2008 | Selkee | |
| 2008/0125853 A1 | 5/2008 | Bailey et al. | |
| 2008/0294230 A1 | 11/2008 | Parker | |
| 2009/0024428 A1 | 1/2009 | Hudock, Jr. | |
| 2009/0069889 A1 | 3/2009 | Suri et al. | |
| 2009/0138079 A1 | 5/2009 | Tuval et al. | |
| 2009/0157175 A1 | 6/2009 | Benichou | |
| 2009/0192585 A1 | 7/2009 | Bloom et al. | |
| 2009/0228093 A1 | 9/2009 | Taylor et al. | |
| 2009/0276040 A1 | 11/2009 | Rowe et al. | |
| 2009/0281619 A1 | 11/2009 | Le et al. | |
| 2009/0299456 A1 | 12/2009 | Melsheimer | |
| 2009/0319037 A1 | 12/2009 | Rowe et al. | |
| 2010/0030318 A1 | 2/2010 | Berra | |
| 2010/0036472 A1 | 2/2010 | Papp | |
| 2010/0036473 A1 | 2/2010 | Roth | |
| 2010/0049313 A1 | 2/2010 | Alon et al. | |
| 2010/0076402 A1 | 3/2010 | Mazzone et al. | |
| 2010/0076541 A1 | 3/2010 | Kumoyama | |
| 2010/0082089 A1 | 4/2010 | Quadri et al. | |
| 2010/0094394 A1 | 4/2010 | Beach et al. | |
| 2010/0121425 A1 | 5/2010 | Shimada | |
| 2010/0145431 A1 | 6/2010 | Wu et al. | |
| 2010/0161036 A1 | 6/2010 | Pintor et al. | |
| 2010/0174363 A1 | 7/2010 | Castro | |
| 2010/0198347 A1 | 8/2010 | Zakay et al. | |
| 2010/0274344 A1 | 10/2010 | Dusbabek et al. | |
| 2011/0015729 A1 | 1/2011 | Jimenez et al. | |
| 2011/0054596 A1 | 3/2011 | Taylor | |
| 2011/0137331 A1 | 6/2011 | Walsh et al. | |
| 2011/0160846 A1 | 6/2011 | Bishop et al. | |
| 2012/0123529 A1 | 5/2012 | Levi et al. | |
| 2012/0239142 A1 | 9/2012 | Liu et al. | |
| 2013/0030519 A1 | 1/2013 | Tran et al. | |
| 2013/0317598 A1 | 11/2013 | Rowe et al. | |
| 2014/0058402 A1 * | 2/2014 | Havel | A61F 2/954 |
| | | | 606/108 |
| 2014/0148889 A1 | 5/2014 | Deshmukh et al. | |
| 2014/0296962 A1 | 10/2014 | Cartledge et al. | |
| 2017/0065415 A1 | 3/2017 | Rupp et al. | |
| 2017/0231756 A1 * | 8/2017 | Armer | A61F 2/2409 |
| | | | 623/2.18 |
| 2018/0153689 A1 | 6/2018 | Maimon et al. | |

(56) References Cited

U.S. PATENT DOCUMENTS

| | | | |
|---|---|---|---|
| 2018/0344456 | A1 | 12/2018 | Barash et al. |
| 2020/0188099 | A1 | 6/2020 | Dvorsky et al. |

FOREIGN PATENT DOCUMENTS

| | | | |
|---|---|---|---|
| EP | 0592410 | B1 | 10/1995 |
| EP | 0850607 | A1 | 7/1998 |
| EP | 2509544 | A1 | 10/2012 |
| EP | 3391857 | A1 | 10/2018 |
| FR | 2815844 | A1 | 5/2002 |
| JP | 2013052281 | A | 3/2013 |
| JP | 2019069241 | A | 5/2019 |
| WO | 9117720 | A1 | 11/1991 |
| WO | 9829057 | A1 | 7/1998 |
| WO | 9912483 | A1 | 3/1999 |
| WO | 0149213 | A2 | 7/2001 |
| WO | 0154625 | A1 | 8/2001 |
| WO | 0176510 | A2 | 10/2001 |
| WO | 0222054 | | 3/2002 |
| WO | 0236048 | A1 | 5/2002 |
| WO | 0247575 | A2 | 6/2002 |
| WO | 02060352 | | 8/2002 |
| WO | 03030776 | A2 | 4/2003 |
| WO | 03047468 | | 6/2003 |
| WO | 2004019825 | A1 | 3/2004 |
| WO | 2005084595 | A1 | 9/2005 |
| WO | 2005102015 | A2 | 11/2005 |
| WO | 2006032051 | A2 | 3/2006 |
| WO | 2006111391 | A1 | 10/2006 |
| WO | 2006138173 | A2 | 12/2006 |
| WO | 2007047488 | A2 | 4/2007 |
| WO | 2007067942 | A1 | 6/2007 |
| WO | 2010121076 | A2 | 10/2010 |
| WO | WO-2011067280 | A1 | 6/2011 |
| WO | WO-2021178634 | A1 | 9/2021 |
| WO | WO-2021257459 | A1 | 12/2021 |

* cited by examiner

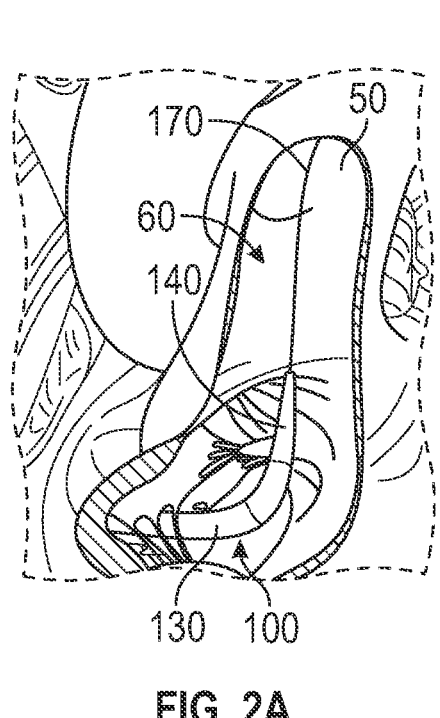
FIG. 2A
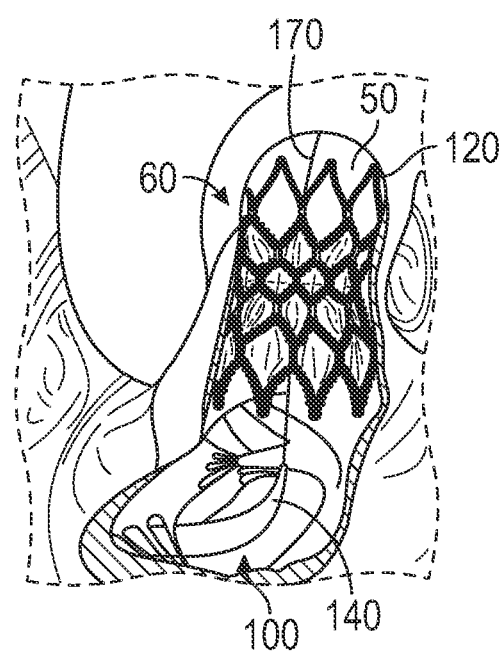
FIG. 2B
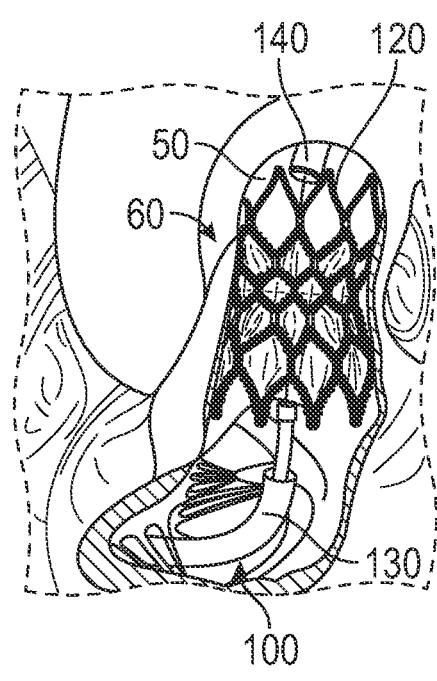
FIG. 2C
FIG. 2D

TRANSCATHETER DELIVERY APPARATUS

CROSS-REFERENCE TO RELATED APPLICATION

This application is a continuation of PCT patent application no. PCT/US2021/058723, filed on Nov. 10, 2021, which claims the benefit of U.S. Provisional Application No. 63/112,326, filed Nov. 11, 2020, each of which is incorporated in its entirety by this specific reference herein.

FIELD

The present disclosure concerns embodiments of delivery apparatus for a transcatheter procedure, such as for transcatheter implantation of a prosthetic device into a patient's vasculature.

BACKGROUND

The human heart can suffer from various valvular diseases. These valvular diseases can result in significant malfunctioning of the heart and ultimately require repair of the native valve or replacement of the native valve with an artificial valve. There are a number of known repair devices (e.g., stents) and artificial valves, as well as a number of known methods of implanting these devices and valves in humans. Percutaneous and minimally-invasive surgical approaches are used in various procedures to deliver prosthetic medical devices to locations inside the body that are not readily accessible by surgery or where access without surgery is desirable. In one specific example, a prosthetic heart valve can be mounted in a crimped state on the distal end of a delivery apparatus and advanced through the patient's vasculature (e.g., through a femoral artery and the aorta) until the prosthetic valve reaches the implantation site in the heart. The prosthetic valve is then expanded to its functional size, for example, by inflating a balloon on which the prosthetic valve is mounted, actuating a mechanical actuator that applies an expansion force to the prosthetic valve, or by deploying the prosthetic valve from a sheath of the delivery apparatus so that the prosthetic valve can self-expand to its functional size. Similar transcatheter procedures can also be used to implant a docking device or a pre-stent within a native valve annulus (e.g., the native mitral valve annulus, native aortic annulus, native pulmonary valve annulus, native tricuspid valve, etc.). A prosthetic valve can be deployed within the docking device and radially expanded so that it can be securely anchored within the docking device. In addition, a transcatheter delivery apparatus can be used to implant a stent (or other prosthesis) into a body duct, such as coronary and/or peripheral vessels, to treat various vascular diseases.

A delivery apparatus needs to have a sufficient strength so that it can be pushed through a patient's vasculature. The delivery apparatus also needs to have a sufficient flexibility so that it can pass through tortuous anatomy of the patient's vasculature. Moreover, the delivery apparatus may contact a prosthetic device during a delivery procedure. As such, the delivery apparatus needs to be configured such that it does not damage or dislocate the prosthesis. Despite their proliferation, typical delivery apparatus have their shortcomings. Accordingly, improvements to delivery apparatus are desirable.

SUMMARY

The present disclosure is directed toward methods and apparatuses relating to apparatus and assemblies for a transcatheter procedure, including specific designs of a nosecone.

Certain embodiments of the disclosure concern an apparatus for a transcatheter procedure. The apparatus can include a shaft having a proximal end, a distal end, and a longitudinal axis extending from the proximal end to the distal end, and a nosecone connected to the distal end of the shaft and comprising a distal portion and a proximal portion. An outer surface of the nosecone can have a cross-sectional profile taken along the longitudinal axis of the shaft. The cross-sectional profile of the proximal portion can include a body region. A slope of the body region can progressively increase from a distal end of the body region to a proximal end of the body region.

Certain embodiments of the disclosure also concern another apparatus for a transcatheter procedure. The apparatus can include a shaft having a proximal end, a distal end, and a longitudinal axis extending from the proximal end to the distal end, and a nosecone connected to the distal end of the shaft and comprising a distal portion and a proximal portion. The proximal portion of the nosecone can include a shoulder region adjacent the distal portion of the nosecone, a connection region connected to the distal end of the shaft, and a body region located between the shoulder region and the connection region. An outer surface of the nosecone can have a cross-sectional profile taken along the longitudinal axis of the shaft. The cross-sectional profile of the body region can include a first section having a first slope, a second section having a second slope, and a third section having a third slope, the first section adjacent the connection region, the third section adjacent the shoulder region, and the second section located between the first section and the second section. The first slope can be greater than the second slope and the third slope, and the second slope can be greater than the third slope.

Certain embodiments of the disclosure also concern a nosecone for a transcatheter delivery apparatus. The nosecone can include a distal portion and a proximal portion, and a longitudinal axis extending from a distal end of the distal portion to a proximal end of the proximal portion. The proximal portion can include a shoulder region adjacent the distal portion of the nosecone and a body region proximal to the shoulder region. An outer surface of the nosecone can have a cross-sectional profile taken along the longitudinal axis of the nosecone. The cross-sectional profile of the body region can have a convex shape when viewed from a centroid of the body region.

Certain embodiments of the disclosure further concern an assembly for a transcatheter procedure. The assembly can include a shaft having a proximal end, a distal end, and a longitudinal axis extending from the proximal end to the distal end, a nosecone connected to the distal end of the shaft and comprising a distal portion and a proximal portion, and a prosthetic implant releasably connected to a distal end portion of the shaft. The proximal portion of the nosecone can include a shoulder region adjacent the distal portion of the nosecone, a connection region connected to the distal end of the shaft, and a body region located between the shoulder region and the connection region. An outer surface of the nosecone can have a cross-sectional profile taken along the longitudinal axis of the shaft. The cross-sectional profile of the body region can have a convex shape when viewed from a centroid of the body region.

The foregoing and other objects, features, and advantages of the disclosure will become more apparent from the following detailed description, which proceeds with reference to the accompanying figures.

BRIEF DESCRIPTION OF THE DRAWINGS

FIG. 2A depicts a distal end portion of the delivery assembly inserted into a patient's vasculature.

FIG. 2B depicts the implant device partially exposed from the delivery apparatus and partially expanded at an implantation site.

FIG. 2C depicts the implant device released from the delivery apparatus and fully expanded at the implantation site.

FIG. 2D depicts the delivery apparatus being withdrawn from the patient's vasculature.

DETAILED DESCRIPTION

General Considerations

Figures 1A, 1B, 1C:
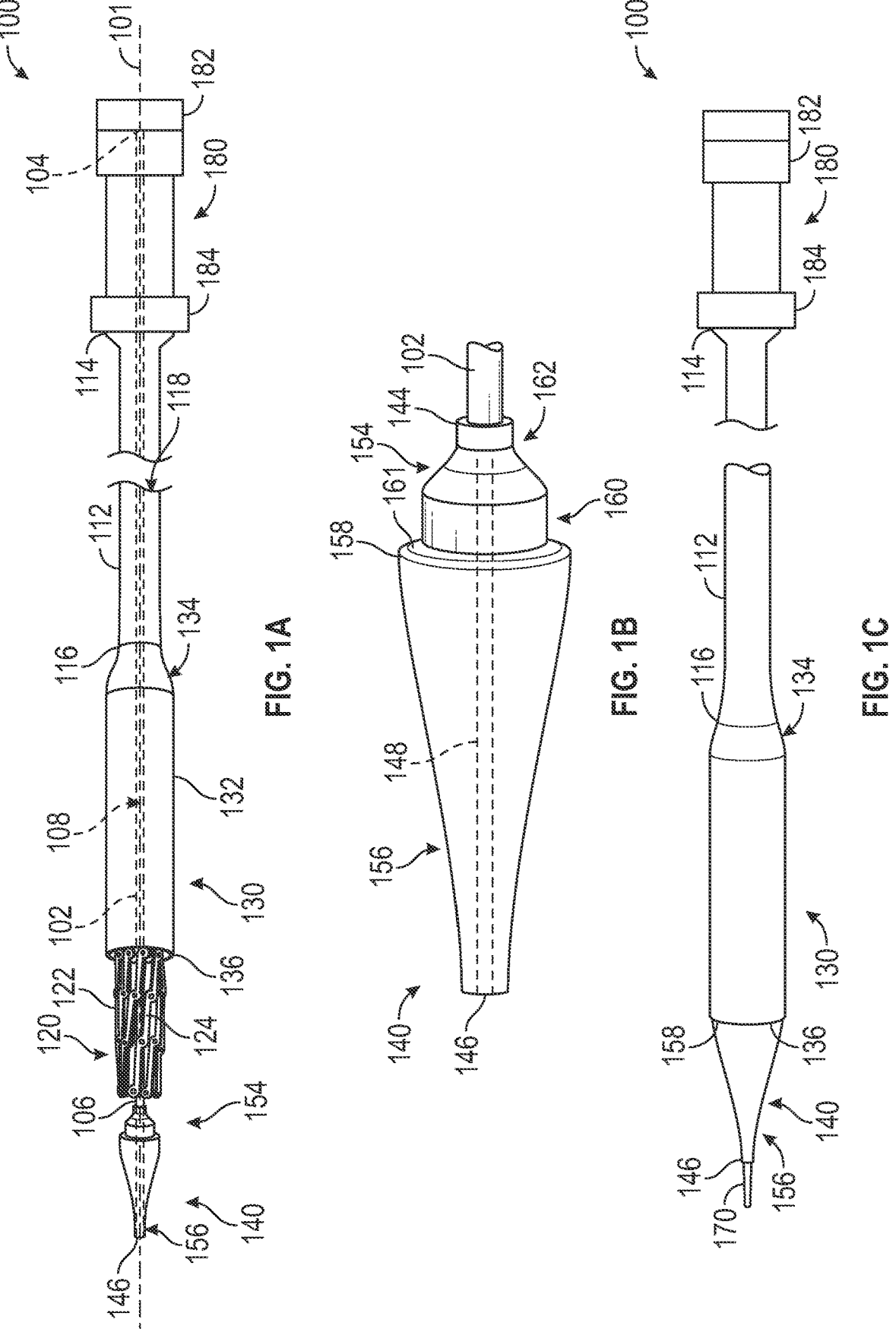
FIG. 1A depicts a partial side view of an exemplary delivery assembly comprising a delivery apparatus and an implant device partially disposed within a delivery sheath of the delivery apparatus.
FIG. 1B depicts a detail view of a nosecone of the delivery apparatus of FIG. 1A.
FIG. 1C depicts a partial side view of the delivery assembly of FIG. 1A, wherein the implant device is fully disposed within the delivery sheath.

It should be understood that the disclosed embodiments can be adapted to deliver and implant prosthetic devices in any of the native annuluses of the heart (e.g., the pulmonary, aortic, mitral, and tricuspid annuluses), and can be used with any of various delivery approaches (e.g., retrograde, antegrade, trans septal, transventricular, transatrial, etc.).

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved. The technologies from any example can be combined with the technologies described in any one or more of the other examples. In view of the many possible embodiments to which the principles of the disclosed technology may be applied, it should be recognized that the illustrated embodiments are only preferred examples and should not be taken as limiting the scope of the disclosed technology.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

As used in this application and in the claims, the singular forms "a," "an," and "the" include the plural forms unless the context clearly dictates otherwise. Additionally, the term "includes" means "comprises." Further, the terms "coupled" and "connected" generally mean electrically, electromagnetically, and/or physically (e.g., mechanically or chemically) coupled or linked and does not exclude the presence of intermediate elements between the coupled or associated items absent specific contrary language.

As used herein, the term "proximal" refers to a position, direction, or portion of a device that is closer to the user and further away from the implantation site. As used herein, the term "distal" refers to a position, direction, or portion of a device that is further away from the user and closer to the implantation site. Thus, for example, proximal motion of a device is motion of the device away from the implantation site and toward the user (e.g., out of the patient's body), while distal motion of the device is motion of the device away from the user and toward the implantation site (e.g., into the patient's body). The terms "longitudinal" and "axial" refer to an axis extending in the proximal and distal directions, unless otherwise expressly defined.

As used herein, the term "approximately" and "about" means the listed value and any value that is within 10% of the listed value. For example, "about 1 mm" means any value between about 0.9 mm and about 1.1 mm, inclusive.

Directions and other relative references (e.g., inner, outer, upper, lower, etc.) may be used to facilitate discussion of the drawings and principles herein, but are not intended to be limiting. For example, certain terms may be used such as "inside," "outside,", "top," "down," "interior," "exterior," and the like. Such terms are used, where applicable, to provide some clarity of description when dealing with relative relationships, particularly with respect to the illustrated embodiments. Such terms are not, however, intended to imply absolute relationships, positions, and/or orientations. For example, with respect to an object, an "upper" part can become a "lower" part simply by turning the object over. Nevertheless, it is still the same part and the object remains the same. As used herein, "and/or" means "and" or "or", as well as "and" and "or."

Overview of Delivery Assembly

FIGS. 1-2 show a delivery assembly, according to one embodiment. The delivery assembly comprises a delivery apparatus 100 and an implant device 120. The delivery apparatus 100 is configured for transcatheter implantation of the implant device 120.

As shown, the delivery apparatus 100 includes a first shaft 102 (also referred to as an "inner shaft," a "guide wire shaft," or a "nosecone shaft") having a proximal end 104, a distal end 106, and a longitudinal axis 101 extending from the proximal end 104 to the distal end 106. In certain embodiments, the inner shaft 102 can have a lumen 108 extending between the proximal end 104 and the distal end 106. The delivery apparatus 100 can also have a second shaft 112 (also referred to as an "outer shaft") extending over the inner shaft 102. For example, the outer shaft 112 can have a lumen 118 extending from a proximal end 114 to a distal end 116 of the outer shaft 112, and the inner shaft 102 can extend through the lumen 118 of the outer shaft 112. In some embodiments, the inner shaft 102 and the outer shaft 112 can be coaxial. In other embodiments, the inner shaft 102 and the outer shaft 112 can be non-coaxial, e.g., the longitudinal axis 101 of the inner shaft can have an offset relative to a longitudinal axis of the outer shaft 112.

As shown in FIG. 1A, an implant device 120 (also referred to as a "prosthetic implant") can be mounted at a distal end portion of the inner shaft 102. As described below, the implant device 120 can be movable between a radially compressed (or "crimped") state and a radially expanded state.

The distal end 106 of the inner shaft 102 can be connected to a nosecone 140. The nosecone 140 can have a proximal end 144 and a distal end 146 (also referred to as a "distal tip"). The proximal end 144 of the nosecone 140 can be secured to the distal end 106 of the inner shaft 102 by any securing means, including thermal bonding, over-molding, gluing, mechanical locking, etc. In certain embodiments, the nosecone 140 can have a lumen 148 extending from the proximal end 144 to the distal end 146 of the nosecone 140. The lumen 148 of the nosecone 140 can linearly connect to the lumen 108 of the inner shaft 102, i.e., the lumen 148 of the nosecone 140 and the lumen 108 of the inner shaft 102 can form a continuous, straight lumen extending from the distal end 106 of the nosecone to the proximal end 104 of the inner shaft 102.

The nosecone 140 can have a proximal portion 154 and a distal portion 156. The distal portion 156 can taper radially outwardly from the distal tip 146 to a proximal end 158 of the distal portion 156. The tapered distal portion 156 can facilitate atraumatic navigation through the patient's vasculature. The proximal portion 154 of the nosecone 140 can have a shoulder region 160 and a body region 162. The shoulder region 160 can have a generally cylindrical shape and have a smaller diameter than the proximal end 158 of the distal portion 156. The body region 162 can taper radially inwardly from a proximal end of the shoulder region 160 to the proximal end 144 of the proximal portion 154. Thus, the proximal end 158 of the distal portion 156 (which also defines the distal end of the shoulder region 160) can define a largest diameter of the nosecone 140. In the embodiment depicted in FIG. 1A, the shoulder region 160 has a step decrease of diameter from the proximal end 158 of the distal portion 156, resulting in a wall 161 that is about perpendicular to the longitudinal axis 101. In addition, when taking a cross-sectional profile of the nosecone 140 along the longitudinal axis 101, a slope of the profile in the proximal portion 154 can have a discontinuity (i.e., a step change) at the boundary between the shoulder region 160 and the body region 162.

In some embodiments, the implant device 120 can be retained in the radially compressed state by a delivery sheath or capsule 130. An axial length of the delivery sheath 130 can be about the same as, or great than, an axial length of the implant device 120 when the implant device 120 is in the radially compressed state. Thus, the delivery sheath 130 can be configured to completely cover the implant device 120 during delivery. In some embodiments, as illustrated in FIGS. 1A-1B, at least a body portion 132 of the delivery sheath 130 can have a larger diameter than the outer shaft 112. A proximal end portion of the delivery sheath 130 can taper radially inwardly and connect to the distal end 116 of the outer shaft 112. In other embodiments, the delivery sheath 130 can have a cylindrical shape and a diameter of the delivery sheath 130 can be about the same as an outer diameter of the outer shaft 112.

In the depicted embodiment, a proximal end portion 134 of the delivery sheath 130 can be connected to the distal end 116 of the outer shaft 112. The proximal end portion 134 of the delivery sheath 130 can be coupled to the distal end 116 of the outer shaft 102 by any known means, including, but not limited to thermal bonding, gluing, mechanical locking, etc. In other embodiments, the delivery sheath 130 can be an integral part of the outer shaft 112. For example, a distal end portion of the outer shaft 112 (which can have a larger diameter, or the same diameter as, the proximal end portion of the outer shaft 112) can retain the implant device 120 in its crimped state and function as the delivery sheath 130.

During delivery, a distal end 136 of the delivery sheath 130 can be configured to abut the shoulder region 160 (e.g., the wall 161) of the nosecone 140 and completely cover the implant device 120. In certain embodiments, as shown in FIG. 1B, a distal end 136 of the delivery sheath 130 and the distal end of the shoulder region have about the same diameter as the proximal end 158 of the distal portion 156 (or the distal end of the shoulder region 160). Thus, an outer surface of the distal portion 156 of the nosecone can have a smooth transition to an outer surface of the delivery sheath 130 when the distal end 136 of the delivery sheath 130 abuts the shoulder region 160 (e.g., the wall 161) of the nosecone 140.

In some embodiments, both the proximal end 104 of the inner shaft 102 and the proximal end 114 of the outer shaft 112 can be connected to a handle 180. In other embodiments, the proximal end 104 of the inner shaft 102 can be coupled to a first handle and the outer shaft 112 can be coupled to a second handle, which is movable relative to the first handle. In some embodiments, the handle 180 can include a drive mechanism 182 (e.g., in the forms of one or more manually rotatable knobs and/or motor-driven actuators) configured to effectuate axial movement of the outer shaft 112 (and the delivery sheath 130 connected thereto) relative to the inner shaft 102. After reaching the target implantation site, the drive mechanism 182 can be actuated to cause the delivery sheath 130 to move proximally relative to the inner shaft 102 and the implant device 120 mounted thereto, thereby causing the implant device 120 to be exposed. In some embodiments, the handle 180 can also include a locking mechanism configured to selectively lock and permit axial movement of the outer shaft 112 (and the delivery sheath 130 connected thereto) relative to the inner shaft 102. Activation of the locking mechanism can prevent premature advancement of the implant device 120 from the delivery sheath 130.

In some embodiments, the handle 180 can further include an adjustment mechanism 184 configured to adjust a curvature of the outer shaft 112. For example, the adjustment mechanism 184 can include one or more rotatable knobs and/or motor-driven actuators that are connected to one or more pull wires connected to a distal end portion of the outer shaft. Thus, by actuating the adjustment mechanism 184, tension in the pull wires can be adjusted so as to steer the distal end portion of the outer shaft 112 in desired angles to facilitate navigation of the delivery apparatus 100 within the patient's vasculature.

Although not shown, it is to be understood that, when the implant device 120 is balloon expandable as described below, the delivery apparatus 100 can further include a third shaft (also referred to as an "intermediate shaft" or a "balloon shaft"). In some embodiments, the balloon shaft can extend over the inner shaft 102 and within the lumen of the 118 of the outer shaft 112. A folded balloon can be mounted on a distal end portion of the balloon shaft and the implant device 120 can be crimped onto the balloon shaft (e.g., onto the folded balloon or at a location adjacent the folded balloon). A proximal end portion of the balloon shaft can also be connected to the handle 180. The implant device 120 can be radially expanded by inflating the balloon, e.g., by injecting an inflation fluid into the balloon through a port located at the proximal end portion of the balloon shaft.

In other embodiments, the implant device 120 can comprise a self-expanding frame or stent. In such embodiments, the implant device 120 can be radially compressed (e.g., with a crimping device) and the radially-compressed implant device 120 can be loaded into a delivery capsule (e.g., a sheath) of a delivery apparatus. The implant device 120 can be radially expanded at or adjacent an implantation location by deploying the implant device 120 from within the delivery capsule, which allows the implant device 120 to radially expand from the delivery configuration to a functional configuration. In some instances, the self-expanding implant device can be further expanded (e.g., during the initial implantation procedure and/or during a subsequent procedure) by an expansion device (e.g., a balloon).

In yet other embodiments, the implant device 120 can comprise a mechanically-expandable frame or stent. In such embodiments, the implant device 120 can be positioned in a radially-compressed configuration (e.g., via actuators of the implant device and/or a crimping device) and releasably coupled to a delivery apparatus. The implant device 120 can be housed in a delivery capsule in some embodiments (e.g., similar to some self-expanding prostheses) or can be exposed on the delivery apparatus (e.g., similar to some balloon-expandable prostheses). Once inserted into the patient's vasculature and positioned at or adjacent an implantation location, the mechanically-expandable implant device can be radially expanded from the radially-compressed configuration to a radially-expanded configuration by actuating one or more actuators of the implant device with the delivery apparatus.

In addition, a guidewire 170 (see e.g., FIG. 1C, 2A) can extend through the lumen of the inner shaft 102 and the lumen 148 of the nosecone 140 such that the inner shaft 102, the outer shaft 112, and the nosecone 140 can be routed over the guidewire 170 to position the implant device 120 at the target implantation site.

Further details on delivery apparatus or systems configured to deliver an implant device to a target implantation, including components of such apparatus or systems (e.g., handle, inner shaft, outer shaft, balloon shaft, etc.), can be found in U.S. Pat. Nos. 9,061,119, 10,363,130, U.S. Patent Publication No. 2018/0263764, and Provisional U.S. Application No. 62/945,039, which are all incorporated by reference herein in their entireties.

Implant Device

In certain embodiments, the implant device 120 can be a prosthetic valve configured to allow the blood to flow through the prosthetic valve in a first direction and prevent the blood from flowing through the prosthetic valve in a second direction that is opposite to the first direction. In certain embodiments, the implant device 120 can be a docking device or a pre-stent configured to receive and retain a prosthetic valve or other implant devices. In certain embodiments, the implant device 120 can be a stent configured to be inserted at least partially within a vessel of a patient's vascular system.

In some embodiments, the implant device 120 can have a frame 122 comprising a plurality of struts 124. The struts 124 can be interconnected to each other at a plurality of junctions 128 to define a plurality of cells and form a lattice structure.

Prior to insertion into a patient, the frame 122 (and thus the implant device 120) can be radially compressed or crimped on the distal end portion of the inner shaft 102, for example, by using a crimping device as described in U.S. Pat. Nos. 7,993,394, 9,277,992, 9,757,232, and 10,010,412, PCT Application No. PCT/US2019/028831, and Provisional U.S. Application Nos. 62/945,039 and 62/876,206, all of which are incorporated by reference herein in their entireties. The frame 122 (and thus the implant device 120) can remain in the radially compressed status, thus keeping a relatively small radial profile, during the implantation procedure.

After reaching the target implantation site, the implant device 120 can be deployed by radially expanding the frame 122. The frame 122 (and thus the implant device 120) can be radially expanded by various means. For example, in one embodiment, the frame 122 can be radially expanded by inflating a balloon of the delivery apparatus, which can be positioned within the frame (e.g., before and/or during the implantation procedure). In another embodiments, the frame 122 can be resilient and self-expanding. For example, the frame 122 can comprise a shape memory material (e.g., Nitinol) so that the frame 122 can expand to its functional size when it is unrestrained by a delivery sheath (e.g., 130). In yet another embodiment, the frame 122 can be mechanically expanded. For example, the struts 124 of the frame 122 can be hingedly connected to each other such that an axial force applied to the frame 122 (e.g., by pressing opposing ends of the frame toward each other) can cause the frame to radially expand. Optionally, the frame 122 can be radially expandable in multiple or a combination of ways (e.g., balloon-expandable, self-expanding, and/or mechanically expandable). Additional details regarding exemplary implant devices having an expandable frame are described in U.S. Pat. Nos. 7,780,723, 9,061,119, 9,393,110, 9,339, 384, 10,363,130, and 10,588,744, U.S. Patent Publication No. 2018/0153689, and 2019/0000615, U.S. Provisional Patent Application No. 62/990,299, which are all incorporated by reference herein in their entireties.

Example Implantation Procedure

As an example, FIG. 2A-2D show a procedure for implanting a prosthetic device at a target implantation site. Specifically, in this example, the prosthetic device is a self-expandable docking device and the target implantation site is the native pulmonary valve of a patient. Similar procedure can be used to deliver and deploy the prosthetic device in any interior surface within the heart or a lumen of the body (e.g., the superior vena cava, the inferior vena cava, the tricuspid valve, the mitral valve, the aortic valve, aorta, etc.).

FIG. 2A shows a guidewire 170 inserted through the patient's vasculature and into the pulmonary bed. Specifically, the guidewire 170 can be advanced to the pulmonary artery 50 by way of the femoral vein, inferior vena cava, right atrium, tricuspid valve, right ventricle, and the right ventricular outflow tract. Under fluoroscopy, the delivery apparatus 100 (only the outer shaft 112, the delivery sheath 130, and the nosecone 140 are shown) that retains the implant device 120 can be delivered over the guidewire 170. The delivery apparatus 100 can be advanced until the implant device 120 reaches an intended landing zone 60 where the implant device 120 is to be deployed.

Then, as shown in FIG. 2B, the outer shaft 112 (and the delivery sheath 130 connected thereto) can be progressively retracted with respect to inner shaft 102 to deploy the implant device 120. As the distal portion of the implant device 120 becomes uncovered by the delivery sheath 130, the distal portion of the frame 122 begins to self-expand. When the frame 122 is partially expanded, the deployment position of the implant device 120 can be reassessed. If repositioning of the implant device 120 is needed, the distal portion of the frame 122 can be compressed and recaptured by the delivery sheath 130 (e.g., by moving the outer shaft 112 distally until it contacts the nosecone 140). Then the implant device 120 can be repositioned within the intended landing zone 60 for redeployment.

Further retracting the outer shaft 112 can uncover the proximal portion of the frame 122 from the delivery sheath 130. The implant device 120 can then be released from the inner shaft 102. Thus, as shown in FIG. 2C, the frame 122 can be fully expanded and frictionally engage the inner wall of the vessel (e.g., pulmonary artery or right ventricular outflow tract), i.e., the implant device 120 is fully deployed at the intended landing zone 60.

As shown in FIG. 2D, after deploying the implant device 120 at the intended landing zone 60, the delivery apparatus 100 can be retracted from the patient's vasculature over the guidewire 170.

Although not shown, it is to be understood that after withdrawing the delivery apparatus 100 from the patient's vasculature, a prosthetic valve can then be delivered to and received by the implant device 120 via another delivery apparatus (which can be the same as or different from 100). In addition, although the implant device 120 is shown to be self-expandable, it is understood that the implant device 120 can also be balloon expandable or mechanically expandable, as described above.

Additional details regarding implantation procedures are described in U.S. Pat. Nos. 10,363,130, and 10,265,169, U.S. Patent Publication No. 2018/0263764, and U.S. Provisional Patent Application No. 63/085,901, which are all incorporated by reference herein in their entireties.

Overview of Nosecone

As described above, the largest diameter of the nosecone 140 is located at the boundary between the proximal portion 154 and the distal portion 156, i.e., the proximal end 158 of the distal portion 156. The distal portion 156 of the nosecone 140 typically tapers radially inwardly toward the distal tip 146 to facilitate atraumatic navigation of the patient's anatomy.

The proximal portion 154 of the nosecone 140 can also gradually reduce in diameter from the largest diameter at the proximal end 158 of the distal portion 156 to a much smaller diameter at the proximal end 144 of the proximal portion 154, which can be about the same as the diameter of the inner shaft 102.

Reduction of diameter in the proximal portion 154 can create the shoulder region 160 including the wall 161, where the distal end 136 of the delivery sheath 130 can abut to retain the implant device 120 in its radially compressed state. The implant device 120 crimped on the distal end portion of the inner shaft 102 can be generally placed proximal to the nosecone 140. In one example embodiment, a distal end of the implant device 120 is adjacent to the proximal end 144 of the nosecone 140. In another embodiment, the distal end of the implant device 120 can overlap at least a portion of the proximal portion 154 of the nosecone 140. The proximal portion 154 of the nosecone 140 desirably has a shorter axial length than the distal portion 156. Reducing the axial length of the proximal portion 154 can allow the implant device 120 to be disposed closer to the distal portion 156 of the nosecone 140. As a result, the delivery sheath 130 can be designed with a shorter axial length while still ensuring it can completely cover the implant device 120 and abut the shoulder region 160 (e.g., the wall 161).

Figure 3:
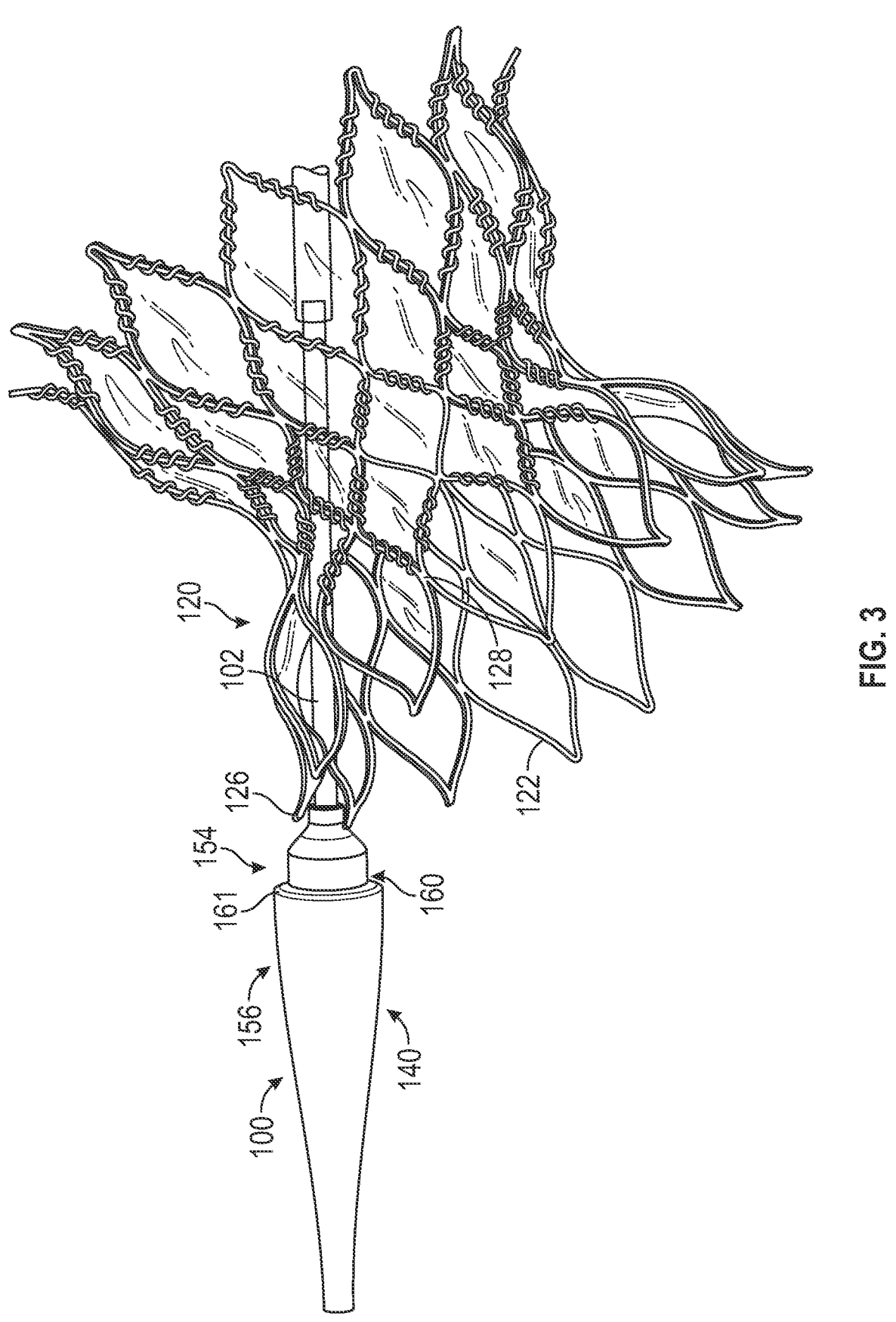
FIG. 3 depicts a nosecone of the delivery apparatus in contact with the prosthetic implant.

When withdrawing the delivery apparatus 100 from the patient's body after the implant device 120 has been deployed, the shoulder region 160 of the nosecone 140 may contact a part or a portion (e.g., frame, commissures, leaflets, skirts, etc.) of the deployed implant device 120. This contact may, at least in part, be a result of the inner shaft and thus the nosecone 140 being non-coaxial with the implant device 120, as depicted in FIG. 3.

Example Nosecones

As described below, a delivery apparatus (such as the delivery apparatus 100) having an improved nosecone design (see, e.g., the nosecones depicted in FIGS. 4A-7C) can, for example, allow the nosecones to be withdrawn smoothly from the deployed implant device. The disclosed nosecones can glide over the components of the implant device even in instances where the inner shaft and nosecone are not coaxial with the implant device.

Geometric Terms

As described herein, a slope of a section (or portion, region, segment, or the like) in a cross-sectional profile of the nosecone taken along a central axis of the nosecone is measured relative to the central axis of the nosecone, e.g., based on an acute angle formed between the section (or portion, region, segment, or the like) and the central axis of the nosecone.

As described herein, a centroid (also referred to as the "geometric center") of an object, including a portion (or section, region, segment, or the like) of the nosecone, is the arithmetic mean position of all the points in the object. When the object has a uniform density, the centroid of the object is also the center of mass of the object. For a portion (or section, region, segment, or the like) of the nosecone that is symmetric about the nosecone's central axis, the centroid of the portion (or section, region, segment, or the like) of the nosecone is typically located on the nosecone's central axis.

As described herein, the cross-sectional profile of the nosecone in a specific region (or portion, section, segment, or the like) has a convex shape relative to a viewpoint (e.g., a centroid of the region) when it curves radially outwardly relative to the central axis of the nosecone, and has a concave shape relative to the viewpoint when it curves radially inwardly relative to the central axis of the nosecone.

As described herein, several types of conic sections, including the ellipse, parabola, and hyperbola, are used to describe the curvature of a section (or portion, region, segment, or the like) in a cross-sectional profile of the nosecone. A conic section is a curve obtained as the intersection of a cutting plane with the surface of a cone. Ellipses arise when the intersection of the cone and the cutting plane is a closed curve. If the cutting plane is parallel to the cone's axis of revolution, then the conic section is a hyperbola. If the cutting plane is parallel to the generating line of the cone, then the conic section is a parabola.

Example Embodiments of Nosecone Shape

FIGS. 4A-4D show a distal end portion of the delivery apparatus 100 having one example embodiment of nosecone 240 that has an improved shape design compared to the nosecone 140 of FIG. 1A. Specifically, the nosecone 240 comprises a proximal portion whose longitudinal cross-sectional profile has a body region corresponding to a parabolic curve.

Similar to 140, the nosecone 240 has a proximal portion 254 and a distal portion 256. The distal portion 256 of the nosecone 240 can taper radially outwardly from a distal end or distal tip 246 of the distal portion 256 to a proximal end 258 of the distal portion 256, and the proximal portion 254 of the nosecone 240 can taper radially inwardly from the proximal end 258 of the distal portion 256 to a proximal end 244 of the proximal portion 254. Thus, the proximal end 258 of the distal portion 256 defines a largest diameter of the nosecone 240. The proximal end 244 of the proximal portion 254 can be connected to the distal end 106 of the inner shaft 102. The longitudinal axis 101 of the inner shaft 102 can be coincident with a central axis 241 of the nosecone 240. In addition, the nosecone 240 can have a lumen 248 extending from the proximal end 244 to the distal tip 246 of the nosecone 240 and linearly connect to the lumen 108 of the inner shaft 102. The proximal portion 254 of the nosecone 240 can also have a shoulder region 260 located proximal to the distal portion 256 and a body region 262 located proximal to the shoulder region 260. However, compared to the nosecone 140, the shoulder region 260 and body region 262 of the nosecone 240 have smoother geometric shapes, as described below.

Figures 4A, 4B, 4C, 4D:
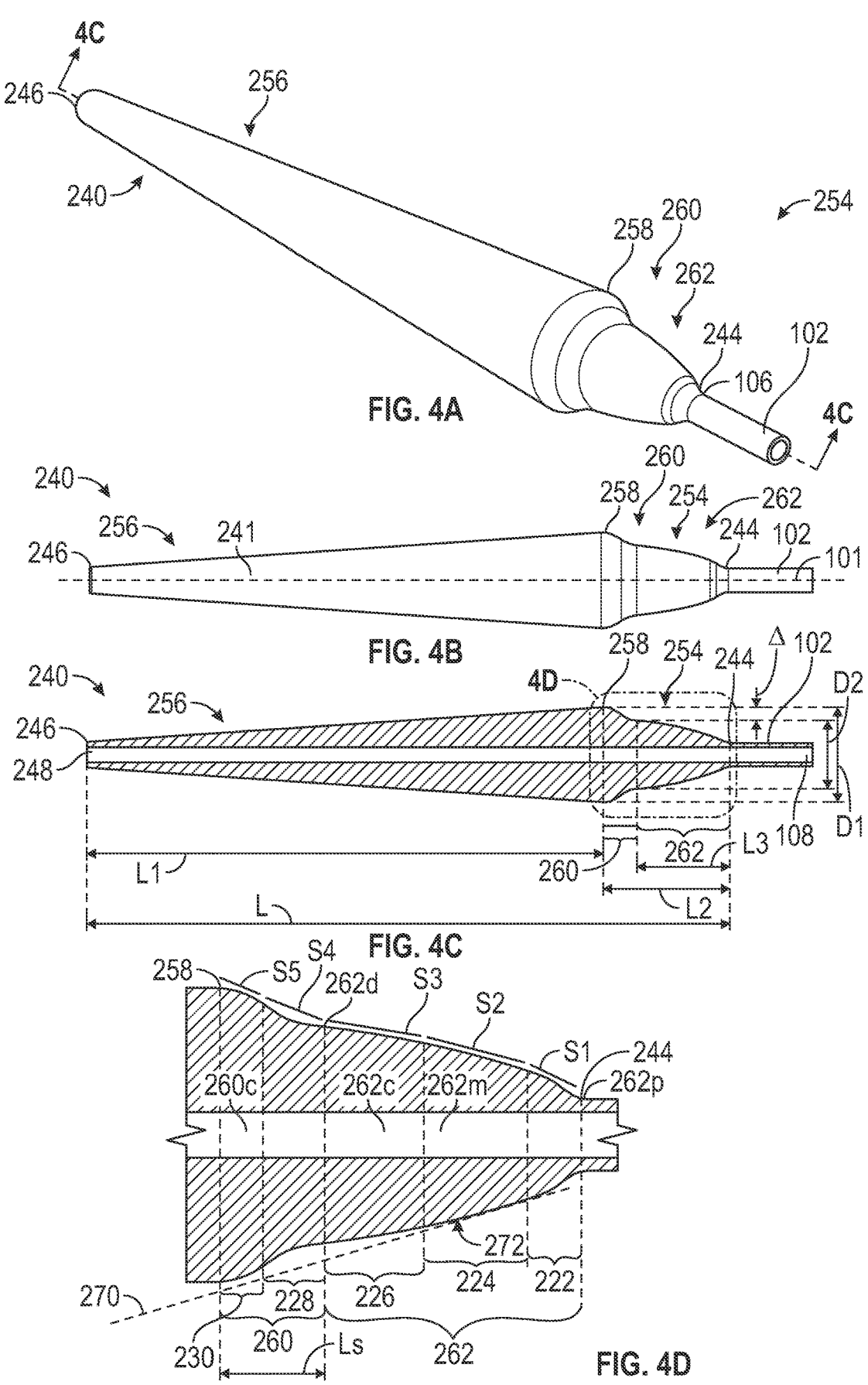
FIG. 4A depicts a perspective view of a distal end portion of a delivery apparatus comprising an inner shaft and one embodiment of a nosecone.
FIG. 4B depicts a side elevation view of the distal end portion of the delivery apparatus of FIG. 4A.
FIG. 4C depicts a cross-sectional view of the distal end portion of the delivery apparatus of FIG. 4A taken along a longitudinal axis of the inner shaft of the delivery apparatus, as depicted by line 4C-4C in FIG. 4A.
FIG. 4D depicts a detail view of a proximal portion of the nosecone depicted in FIG. 4C.

As shown in FIGS. 4C-4D, the body region 262 can have a nonlinear, or curved cross-sectional profile. Specifically, the cross-sectional profile of the body region 262 can have a convex shape relative to a centroid 262c of the body region 262. In one embodiment, the convex shape of the body region 262 can be defined by a parabolic curve. In another embodiment, the convex shape of the body region 262 can be defined by a hyperbolic curve. In yet another embodiment, the convex shape of the body region 262 can be defined by an elliptical curve.

The slope of the body region 262 can progressively increases from a distal end 262d of the body region 262 to a proximal end 262p of the body region 262 (the proximal end 262p of the body region 262 is also the proximal end 244 of the proximal portion 254 in this example). For example, the body region 262 can include a first section 222 having a first slope S1, a second section 224 having a second slope S2, and a third section 226 having a third slope S3. As shown in FIGS. 4C-4D, the first section 222 is adjacent to the distal end 106 of the inner shaft 102, the third section 226 is adjacent to the shoulder region 260, and the second section 224 is located between the first section 222 and the third section 226. The first slope S1 can be greater than the second slope S2 and the third slope S3, and the second slope S2 can be greater than the third slope S3.

As shown, the shoulder region 260 can also have a nonlinear, or curved cross-sectional profile. Specifically, the shoulder region 260 can have a peak portion 230 connected to the distal portion 256 of the nosecone 240 and a valley portion 228 connected to the distal end 262d of the body region 262. A diameter of the shoulder region 260 can progressively decrease from the peak portion 230 to the valley portion 228.

In certain embodiments, the valley portion 228 can have a fourth slope S4 and the peak portion 230 can have has a fifth slope S5. The fourth slope S4 can be about the same as or less than the third slope S3. In some embodiments, the fourth slope S4 can be smaller than the fifth slope S5. In some embodiments, the boundary between the peak portion 230 and the valley portion 228 can have the largest slope of the shoulder region 260.

As described herein, when comparing the slopes (e.g., S1-S5) in different sections or portions, the slope in each section or portion is measured in the same way. For example, in one embodiment, the slope of a section or portion is measured as an average slope in that section or portion. In another embodiment, the slope of a section or portion is measured as a median slope in that section or portion. In yet another embodiment, the slope of a section or portion is measured as a maximum slope in that section or portion. In yet a further embodiment, the slope of a section or portion is measured as a minimum slope in that section or portion.

In certain embodiments, the cross-sectional profile of the proximal portion 254 in the valley portion 228 can have a concave shape relative to a centroid 260c of the shoulder region 260, and the cross-sectional profile of the proximal portion 254 in the peak portion 230 can have a convex shape relative to the centroid 260c of the shoulder region 260. The respective concave or convex shape of the valley portion 228 and the peak portion 230 can, for example, be defined by a parabolic curve, a hyperbolic curve, or an elliptical curve. In other embodiments, the cross-sectional profile of the shoulder region 260 (including both the peak portion 230 and the valley portion 228) can have a concave shape relative to the centroid 260c of the shoulder region 260. The concave shape of the shoulder region 260 can, for example, be defined by a parabolic curve, a hyperbolic curve, or an elliptical curve.

In certain embodiments, the peak portion 230 of the shoulder region 260 can be configured to engage a distal end of a delivery sheath. For example, during delivery of the implant device 120, the distal end 136 of the delivery sheath 130 can be configured to press against the peak portion 230 of the shoulder region 260 to retain the implant device 120 in its radially compressed state.

In certain embodiments, the cross-sectional profile of the distal portion 256 can linearly connect the distal end 246 of the distal portion 256 to the proximal end 258 of the distal portion 256. For example, as shown in FIG. 4C, the line connecting the distal end 246 and the proximal end 258 in the cross-sectional profile of the distal portion 256 is substantially straight.

FIGS. 5A-5D show a distal end portion of the delivery apparatus 100 having another example embodiment of nosecone 340. Specifically, the nosecone 340 comprises a proximal portion whose longitudinal cross-sectional profile has a body region corresponding to a parabolic curve and a connection region corresponding to an elliptical curve.

Similar to 240, the nosecone 340 has a proximal portion 354 and a distal portion 356. A proximal end 358 of the distal portion 356 can define a largest diameter of the nosecone 340. A proximal end 344 of the proximal portion 354 can be connected to the distal end 106 of the inner shaft 102. The longitudinal axis 101 of the inner shaft 102 can coincide with a central axis 341 of the nosecone 340. In addition, the nosecone 340 can have a lumen 348 extending from the proximal end 344 to a distal tip 346 of the nosecone 340 and linearly connect to the lumen 108 of the inner shaft 102.

Figures 5A, 5B, 5C, 5D:
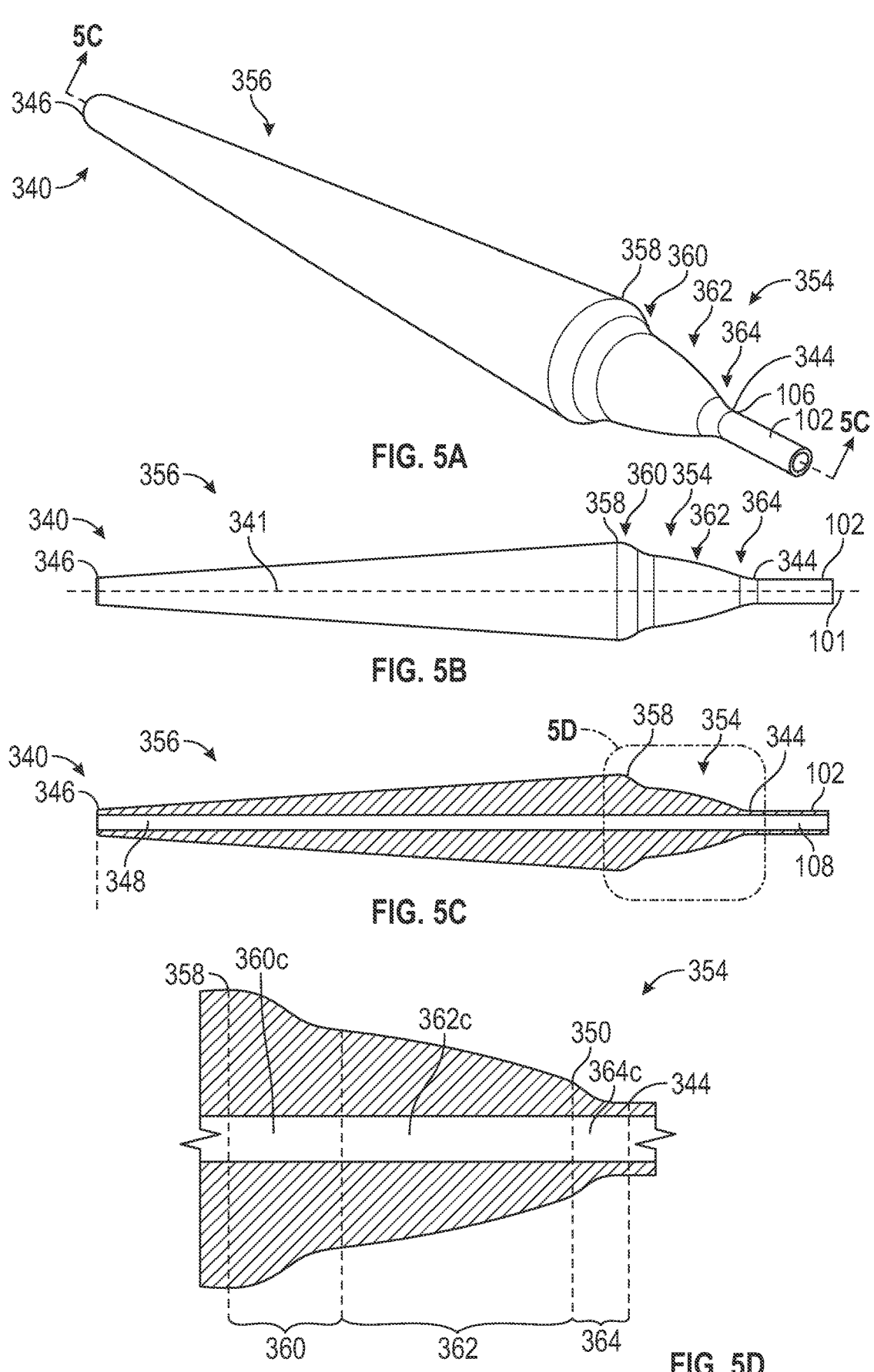
FIG. 5A depicts a perspective view of a distal end portion of a delivery apparatus comprising an inner shaft and another embodiment of a nosecone.
FIG. 5B depicts a side elevation view of the distal end portion of the delivery apparatus of FIG. 5A.
FIG. 5C depicts a cross-sectional view of the distal end portion of the delivery apparatus of FIG. 5A taken along a longitudinal axis of the inner shaft of the delivery apparatus, as depicted by line 5C-5C in FIG. 5A.
FIG. 5D depicts a detail view of a proximal portion of the nosecone depicted in FIG. 5C.

As shown in FIGS. 5C-5D, the proximal portion 354 of the nosecone 340 can also have a shoulder region 360 located proximal to the distal portion 356 and a body region 362 located proximal to the shoulder region 360. However, compared to the nosecone 240, the proximal portion 354 of the nosecone 340 can have an additional connection region 364 located between the body region 362 and the inner shaft 102, e.g., the connection region 364 can connect a proximal end 350 of the body region 362 to the distal end 106 of the inner shaft 102.

In some embodiments, the distal portion 356, the shoulder region 360, and the body region 362 of the nosecone 340 can have about the same geometric shapes as the distal portion 256, the shoulder region 260, and the body region 262 of the nosecone 240, respectively. For example, the cross-sectional profile of the body region 362 can have a convex shape relative to a centroid 362c of the body region 362, and the cross-sectional profile of the shoulder region 360 can have a concave shape relative to a centroid 360c of the shoulder region 360.

In some embodiments, the cross-sectional profile of the proximal portion 354 in the connection region 364 can have a different curvature than the body region 362. For example, in one embodiment, the cross-sectional profile of the connection region 364 can have a concave shape relative to a centroid 364c of the connection region 364 (in contrast to the convex shape in the body region 362). The concave shape of the connection region 364 can be defined by a parabolic curve, a hyperbolic curve, or an elliptical curve. In another example, the cross-sectional profile of the connection region 364 can linearly connect the proximal end 350 of the body region 362 to the distal end 106 of the inner shaft 102 (i.e., forming a substantially straight line between the proximal end 350 of the body region 362 and the distal end of the inner shaft 102).

In some embodiments, the cross-sectional profile of the connection region 364 can also have a convex shape (e.g., defined by a parabolic curve, a hyperbolic curve, or an elliptical curve) relative to the centroid 364c of the connection region 364. The convex shape of the connection region 364 can be the same as, or different from, the convex shape of the body region 362. In one specific embodiment, the cross-sectional profile of the body region 362 and the connection region 364 can form a continuous convex shape relative to the centroid 362c of the body region 362. In that case, the connection region 364 merges into the body region 362. In other words, the proximal portion 254 depicted in FIG. 4C-4D can be considered as a special case of the proximal portion 354 depicted in FIGS. 5C-5D where the cross-sectional profile of the connection region 364 and the body region 362 have the same curvature.

Figure 6A:
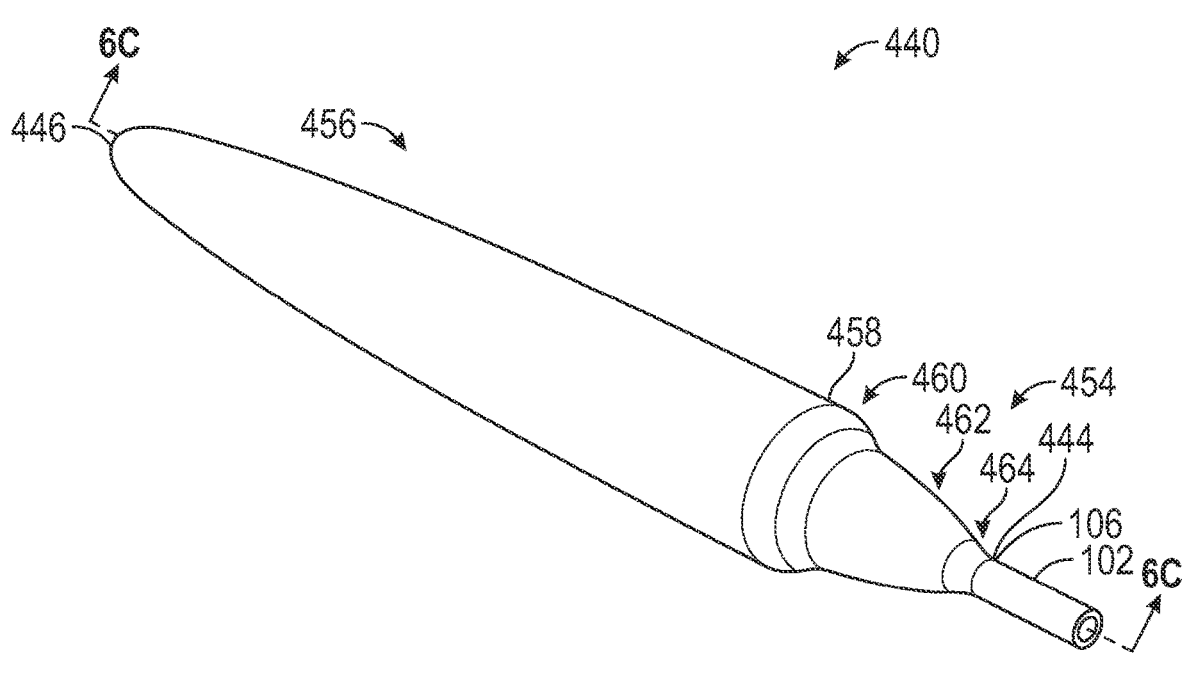
FIG. 6A depicts a perspective view of a distal end portion of a delivery apparatus comprising an inner shaft and yet another embodiment of a nosecone.
Figure 6B:
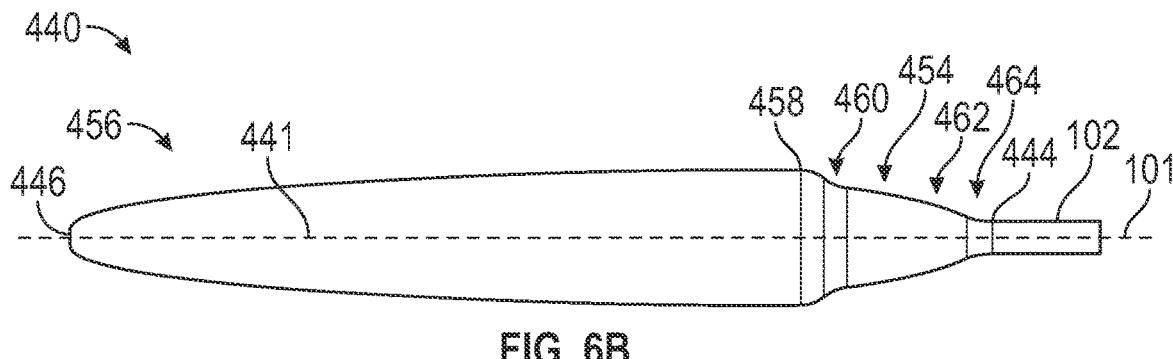
FIG. 6B depicts a side elevation view of the distal end portion of the delivery apparatus of FIG. 6A.
Figure 6C:
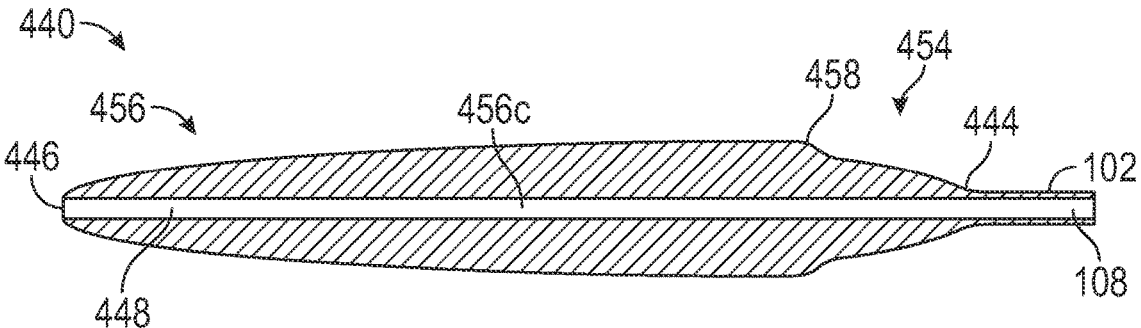
FIG. 6C depicts a cross-sectional view of the distal end portion of the delivery apparatus of FIG. 6A taken along a longitudinal axis of the inner shaft of the delivery apparatus, as depicted by line 6C-6C in FIG. 6A.

FIGS. 6A-6C show a distal end portion of the delivery apparatus 100 having another example embodiment of nosecone 440. Specifically, the nosecone 440 comprises a proximal portion similar to 354 as depicted in FIGS. 5A-5D and a distal portion whose longitudinal cross-sectional profile corresponds to an elliptical curve.

Similar to 340, the nosecone 440 has a proximal portion 454 and a distal portion 456. A proximal end 458 of the distal portion 456 can define a largest diameter of the nosecone 440. A proximal end 444 of the proximal portion 454 can have a shoulder region 460 located proximal to the distal portion 456, a body region 462 located proximal to the shoulder region 460, and a connection region 464 located between the body region 462 and the inner shaft 102. The longitudinal axis 101 of the inner shaft 102 can coincide with a central axis 441 of the nosecone 440. The nosecone 440 can also have a lumen 448 extending from the proximal end 444 to a distal tip 446 of the nosecone 440 and linearly connect to the lumen 108 of the inner shaft 102.

In some embodiments, the proximal portion 454 (including the shoulder region 460, the body region 462, and the connection region 464) can have about the same geometric shape as the proximal portion 354 of the nosecone 340. However, in contrast to the distal portion 356 of the nosecone 340 which has a liner cross-sectional profile, the distal portion 456 of the nosecone 440 can have a nonlinear, or curved cross-sectional profile.

For example, in the depicted example, the cross-sectional profile of the distal portion 456 has a convex shape relative to a centroid 456c of the distal portion 456. In one embodiment, the convex shape of the distal portion 456 can be defined by a parabolic curve. In another embodiment, the convex shape of the distal portion 456 can be defined by a hyperbolic curve. In yet another embodiment, the convex shape of the distal portion 456 can be defined by an elliptical curve.

Figure 7A:
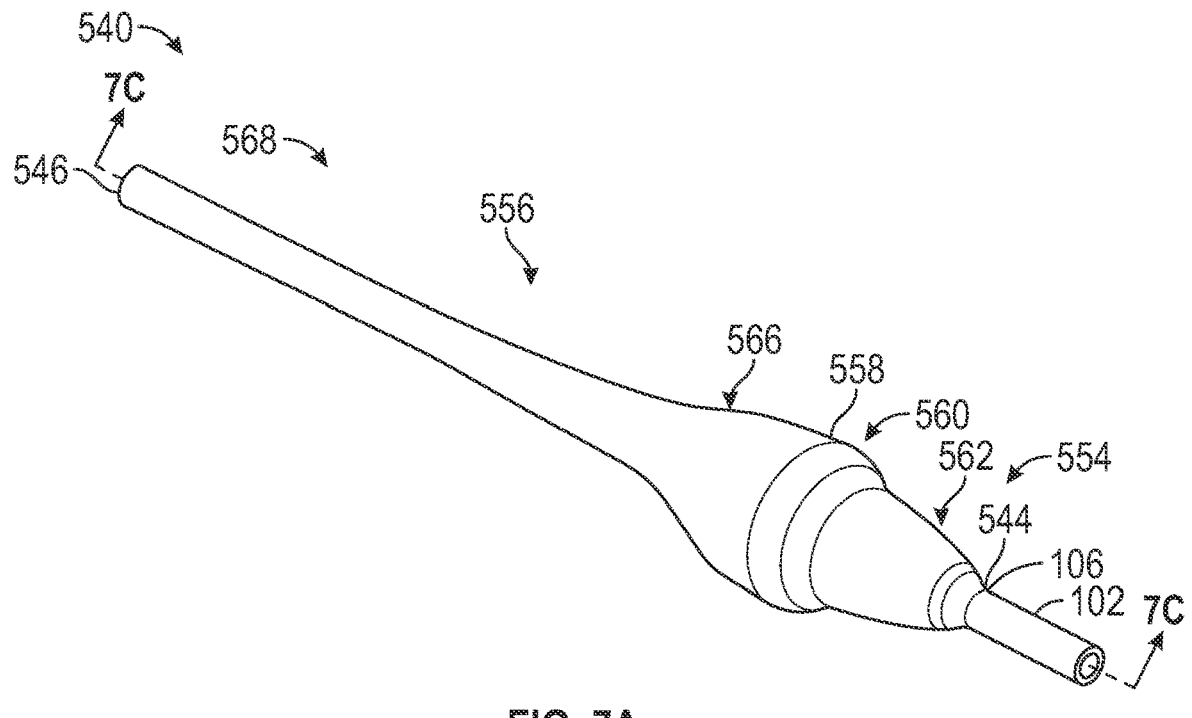
FIG. 7A depicts a perspective view of a distal end portion of a delivery apparatus comprising an inner shaft and a further embodiment of a nosecone.
Figure 7B:
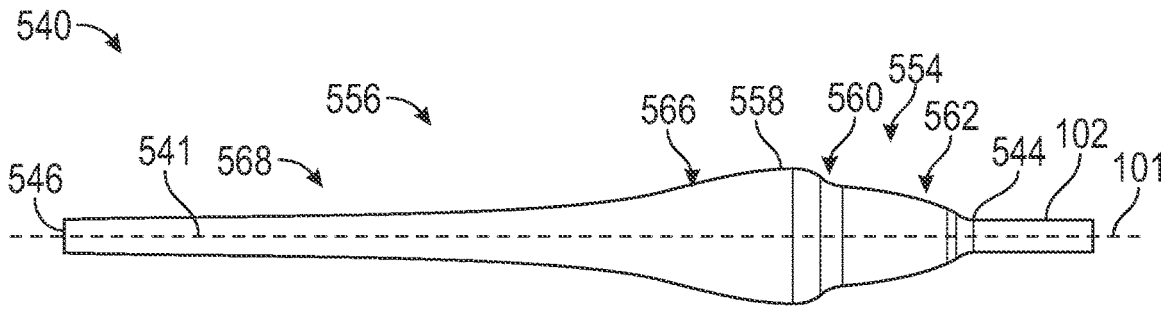
FIG. 7B depicts a side elevation view of the distal end portion of the delivery apparatus of FIG. 7A.
Figure 7C:
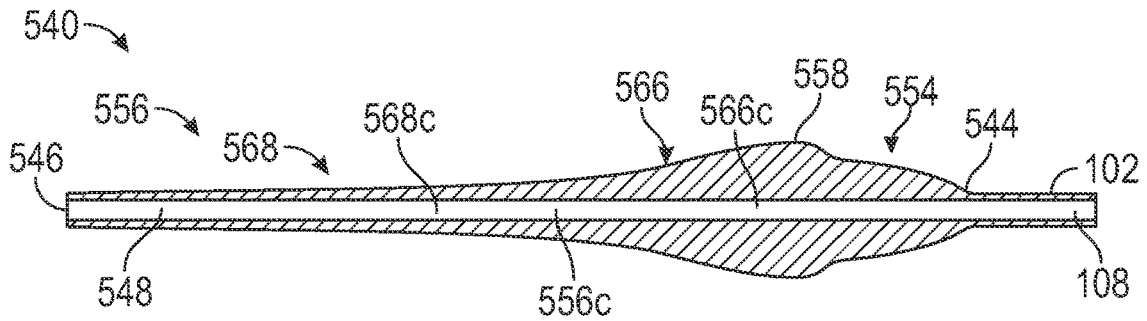
FIG. 7C depicts a cross-sectional view of the distal end portion of the delivery apparatus of FIG. 7A taken along a longitudinal axis of the inner shaft of the delivery apparatus, as depicted by line 7C-7C in FIG. 7A.

FIGS. 7A-7C show a distal end portion of the delivery apparatus 100 having yet another example embodiment of nosecone 540. Specifically, the nosecone 540 comprises a proximal portion similar to 254 as depicted in FIGS. 4A-4D and a distal portion comprising two sections with different curvatures.

Similar to 240, the nosecone 540 has a proximal portion 554 and a distal portion 556. A proximal end 558 of the distal portion 556 can define a largest diameter of the nosecone 540. The proximal portion 554 can have a shoulder region 560 located proximal to the distal portion 556 and a body region 562 located proximal to the shoulder region 560. The longitudinal axis 101 of the inner shaft 102 can coincide with a central axis 541 of the nosecone 540. The nosecone 540 can also have a lumen 548 extending from the proximal end 544 to a distal tip 546 of the nosecone 540 and linearly connect to the lumen 108 of the inner shaft 102.

In some embodiments, the proximal portion 554 (including the shoulder region 560 and the body region 562) can have about the same geometric shape as the proximal portion 254 of the nosecone 240. However, in contrast to the distal portion 256 of the nosecone 240 which has a liner cross-sectional profile, the distal portion 556 of the nosecone 440 can have a nonlinear, or curved cross-sectional profile.

For example, in certain embodiments, the cross-sectional profile of the distal portion 556 can have a concave shape relative to a centroid 556c of the distal portion 556. The concave shape of the distal portion 556 can be defined by a parabolic curve, a hyperbolic curve, or an elliptical curve.

In other embodiments, the distal portion 556 can include multiple sections and each section can have its own curvature. For example, the distal portion 556 can have a tip section 568 and a body section 566 located proximal to the tip section 568. In one example embodiment, the tip section 568 can have a concave shape relative to a centroid 568c of the tip section 568, and the body section 566 can have a convex shape relative to a centroid 566c of the body section 566. The respective concave or convex shape of the tip section 568 and the body section 566 can be defined by a parabolic curve, a hyperbolic curve, or an elliptical curve. In yet another embodiment, the tip section 568 can have a linear cross-sectional profile and the body section 566 can have a nonlinear cross-sectional profile (e.g., convex shape, or mixed convex and concave shape, etc.).

Example Embodiments of Nosecone Dimensions

Dimensions of different portions (or sections, segments, regions, or the like) of the nosecones described above can be configured to maintain an overall small profile of the nosecone while improving the ability of the nosecone to be withdrawn smoothly from the implant device during the delivery procedure. The nosecone dimensions are described below using the nosecone 240 and 340 as examples, although it is to be understood that similar dimensions can be applied to the nosecone 440 and 540 described above.

For example, the dimensions of the shoulder region (e.g., 260) can be configured to ensure the nosecone can both engage a distal end of the delivery sheath during delivery of the implant device and be smoothly withdrawn from the implant device after the implant device has been deployed.

On one hand, the slope (e.g., S5) of the peak portion (e.g., 230) of the shoulder region can be sufficiently large so that the peak portion can resist the delivery sheath 130 from moving distally and past the peak portion. On the other hand, the slope (e.g., S5) of the peak portion (e.g., 230) can be much smaller than 90 degrees so that the peak portion can slide along the implant device 120 when withdrawing the delivery apparatus.

In certain embodiments, the slope (e.g., S5) of the peak portion (e.g., 230) can range from about 0 degrees to about 65 degrees, or between about 0 degrees and about 45 degrees. In certain embodiments, the slope (e.g., S4) of the valley portion (e.g., 228) can range from about 0 degrees to about 65 degrees, or between about 0 degrees and about 45 degrees. In certain embodiments, the largest slope of the cross-sectional profile of the shoulder region (e.g., 260) can range from about 15 degrees to about 65 degrees. In one specific embodiment, the largest slope of the cross-sectional profile of the shoulder region is about 40 degrees.

The slope (or slope range) of the shoulder region (e.g., 260) is affected by both the axial length of the shoulder region and the radial depth of the shoulder region (also referred to as the "shoulder depth"). As noted above, the proximal end (e.g., 258) of the distal portion (e.g., 256) can define the largest diameter of the nosecone, denoted as D1 in FIG. 4C. The distal end (e.g., 262d) of the body region (e.g., 262) of the proximal portion (e.g., 254) can define another diameter, denoted as D2 in FIG. 4C. The shoulder depth, denoted as $\Delta$ in FIG. 4C, can be defined as half of the difference between D1 and D2, i.e., $\Delta = (D1-D2)/2$. The axial length of the shoulder region (e.g., 260), denoted as Ls in FIG. 4D, can be measured as the axial length between the proximal end (e.g., 258) of the distal portion (e.g., 256) and the distal end (e.g., 262d) of the body region (e.g., 262).

In certain embodiments, the shoulder region (e.g., 260) can have an axial length Ls ranging from about 1 mm to about 10 mm. In one specific embodiment, the axial length of the shoulder region Ls is about 2.5 mm.

In certain embodiments, the shoulder depth $\Delta$ can range from about 0.1 mm to about 2.5 mm. In one specific embodiment, the shoulder depth $\Delta$ is about 1.0 mm.

In certain embodiments, a ratio of the shoulder depth to an axial length of the shoulder region, i.e., $\Delta/Ls$, can range from about 0.02 to about 2.50. In one specific embodiment, the ratio $\Delta/Ls$ is about 0.40.

In certain embodiments, the ratio D2/D1 can range from about 0.50 to about 0.96. In one specific embodiment, the ratio D2/D1 is about 0.75.

As described herein, the dimensions and/or shape of the body region (e.g., 262) can also be configured in conjunction with the configuration of the shoulder region (e.g., 260). For example, the slope of the proximal portion 254 (in the cross-sectional profile) can be configured to vary (e.g., increase or decrease) progressively. In other words, the slope of the proximal portion 254 can vary continuously without a step change. Accordingly, not only is there no abrupt change of diameter in the shoulder region 260 or the body region 262, but there is also no abrupt change of diameter at the boundary between the distal portion 256 and the shoulder region 260, or at the boundary between the shoulder region 260 and the body region 262.

In addition, as illustrated in FIG. 4D, the slope of the body region 262 can be so configured that the cross-sectional profile of the body region 262 can include at least a section 272 with a relatively large slope, wherein a tangent line 270 at the section 272 does not intercept the cross-sectional profile of the shoulder region 260 (including its distal end, which is also the proximal end 258 of the distal portion 256). In certain embodiments, the section 272 can extend from the proximal end 262p of the body region 262 to a mid-point 262m of the body region 262. For example, the section 272 can be located within the first section 222 or the second section 224. In other embodiments, the section 272 can extend from the mid-point 262m of the body region 262 to the distal end 262d of the body region. For example, the section 272 can be located within the second section 224 or the third section 226.

As noted above in reference to FIG. 3, retracting the delivery apparatus may cause an apex 126 and/or a junction 128 of the annular frame 122 of the implant device 120 to contact the proximal portion 254 of the nosecone 240. The nosecone design described above can, among other things, improve the ease in which the nosecone can be withdrawn from the deployed implant device. Specifically, the gradual reduction (instead of step reduction) of the diameter and continuous variation (instead of step change) of slope in the proximal portion 254 can cause the apex 126 and/or junction 128 of the frame 122 to slide smoothly along the outer surface of the proximal portion 254 without being obstructed by any portion of the nosecone 240 when retracting the delivery apparatus. In addition, because of the relatively large slope at the section 272, further retracting the delivery apparatus 100 in the proximal direction can, for example, deflect the frame 122 and cause the frame 122 to slide along the tangent line 270 (which extends radially away from the shoulder region 260) in the distal direction relative to the nosecone 240. As a result, the shoulder region 260 of the nosecone 240 can glide smoothly along the frame as the nosecone 240 is retracted through a lumen of the frame 122.

The overall slope of the body region (e.g., 262) can be affected by an axial length of the body region (denoted as L3 in FIG. 4C) and the diameter D2 at the distal end (e.g., 262*d*) of the body region. In certain embodiments, the axial length of the body region L3 can range from about 2 mm to about 20 mm. In one specific embodiment, the axial length of the body region L3 is about 5.5 mm.

When the proximal portion (e.g., 354) of the nosecone has a connection region (e.g., 364), the dimensions of the connection region can be similarly configured in conjunction with the configuration of the shoulder region (e.g., 360) and the body region (e.g., 362).

For example, in certain embodiments, a largest slope of the cross-sectional profile of the connection region (e.g., 364) can range from about 20 degrees to about 65 degrees. In one specific embodiment, the largest slope of the cross-sectional profile of the connection region (e.g., 364) is about 40 degrees.

In certain embodiments, the connection region (e.g., 364) can have an axial length ranging from about 0.1 mm to about 5.0 mm. In one specific embodiment, the axial length of the connection region (e.g., 364) is about 1.0 mm.

In addition, certain dimensions of the distal portion of the nosecone can also be configured to reduce the overall profile of the nosecone and facilitate atraumatic navigation within the patient's vasculature.

The axial length of the nosecone (denoted as L) is the sum of the axial length of the distal portion (denoted as L1) and the axial length of the proximal portion (denoted as L2), as illustrated in FIG. 4C.

In certain embodiments, the axial length of the distal portion (e.g., 256) can range from about 10 mm to about 80 mm. In one specific embodiment, the axial length of the distal portion L1 is about 35 mm.

In certain embodiments, a ratio of the axial length of the proximal portion to the axial length of the distal portion, i.e., L2/L1, can range from about 0.03 to about 1.00. In one specific embodiment, the ratio L2/L1 is about 0.25.

In certain embodiments, a ratio of the axial length of the nosecone to the maximum diameter of the nosecone, i.e., L/D1 ranges from about 1.5 to about 20.0. In one specific embodiment, the ratio L/D1 is about 6.5.

In certain embodiments, a ratio of the axial length of the body region to the axial length of the distal portion, i.e., L3/L1, can range from about 0.02 to about 0.95. In one specific embodiment, the ratio L3/L1 is about 0.20.

It is to be understood that various nosecone shapes described above and shown in FIGS. 4-7 are merely exemplary. Other variations of the nosecone shape based on the same principles disclosed herein are within the scope of the invention. For example, the overall curvatures of the proximal portion and/or the distal portion, the number and shape of different regions/sections within the proximal and/or distal portion (e.g., the shoulder region, the body region, the connection region, etc.), the axial lengths of different portions (or segments, sections, regions, or the like) and/or their relative ratios, the diameter of different portions (or segments, sections, regions, or the like) and/or their relative ratios, etc., can be varied to maintain the overall small profile (e.g., in terms of diameter and axial length) of the nosecone while improving the ability of the nosecone of the delivery apparatus to be withdrawn from the patient's vasculature after deployment of the implant device.

EXEMPLARY EMBODIMENTS

In view of the above-described implementations of the disclosed subject matter, this application discloses the additional examples enumerated below. It should be noted that one feature of an example in isolation or more than one feature of the example taken in combination and, optionally, in combination with one or more features of one or more further examples are further examples also falling within the disclosure of this application.

Example 1. An apparatus for a transcatheter procedure, the apparatus comprising:

a shaft having a proximal end, a distal end, and a longitudinal axis extending from the proximal end to the distal end; and a nosecone connected to the distal end of the shaft and comprising a distal portion and a proximal portion, wherein an outer surface of the nosecone has a cross-sectional profile taken along the longitudinal axis of the shaft, wherein the cross-sectional profile of the proximal portion comprises a body region, wherein a slope of the body region progressively increases from a distal end of the body region to a proximal end of the body region.

Example 2. The apparatus of any example herein, particularly example 1, wherein the body region has a convex shape relative to a centroid of the body region.

Example 3. The apparatus of any example herein, particularly example 2, wherein the convex shape of the body region is defined by a parabolic curve.

Example 4. The apparatus of any example herein, particularly example 2, wherein the convex shape of the body region is defined by a hyperbolic curve.

Example 5. The apparatus of any example herein, particularly example 2, wherein the convex shape of the body region is defined by an elliptical curve.

Example 6. The apparatus of any example herein, particularly any one of examples 1-5, wherein an axial length of the body region ranges from about 2 mm to about 20 mm.

Example 7. The apparatus of any example herein, particularly example 6, wherein the axial length of the body region is about 5.5 mm.

Example 8. The apparatus of any example herein, particularly any one of examples 1-7, wherein the cross-sectional profile of the proximal portion further comprises a connection region located between body region and the distal end of the shaft.

Example 9. The apparatus of any example herein, particularly example 8, wherein the cross-sectional profile of the proximal portion in the connection region has a concave shape relative to a centroid of the connection region.

Example 10. The apparatus of any example herein, particularly example 8, wherein the cross-sectional profile of the proximal portion in the connection region linearly connects the proximal end of the body region to the distal end of the shaft.

Example 11. The apparatus of any example herein, particularly any one of examples 8-10, wherein the connection region has an axial length ranging from about 0.1 mm to about 5.0 mm.

Example 12. The apparatus of any example herein, particularly example 11, wherein the axial length of the connection region is about 1.0 mm.

Example 13. The apparatus of any example herein, particularly any one of examples 1-12, wherein the cross-sectional profile of the proximal portion further comprises a shoulder region located between the body region and the distal portion of the nosecone.

Example 14. The apparatus of any example herein, particularly example 13, wherein the shoulder region comprises a peak portion connected to the distal portion of the nosecone and a valley portion connected to the distal end of the body region, wherein a diameter of the shoulder region progressively decreases from the peak portion to the valley portion.

Example 15. The apparatus of any example herein, particularly example 14, wherein the cross-sectional profile of the proximal portion in the valley portion has a concave shape relative to a centroid of the shoulder region and the cross-sectional profile of the proximal portion in the peak portion has a convex shape relative to the centroid of the shoulder region.

Example 16. The apparatus of any example herein, particularly any one of examples 13-15, wherein the shoulder region has an axial length ranging from about 1 mm to about 10 mm.

Example 17. The apparatus of any example herein, particularly example 16, wherein the axial length of the shoulder region is about 2.5 mm.

Example 18. The apparatus of any example herein, particularly any one of examples 1-17, wherein the cross-sectional profile of the distal portion linearly connects a distal end of the distal portion to a proximal end of the distal portion.

Example 19. The apparatus of any example herein, particularly any one of examples 1-17, wherein the cross-sectional profile of the distal portion has a convex shape relative to a centroid of the distal portion.

Example 20. The apparatus of any example herein, particularly example 19, wherein the convex shape of the distal portion is defined by an elliptical curve.

Example 21. The apparatus of any example herein, particularly example 19, wherein the convex shape of the distal portion is defined by a parabolic curve.

Example 22. The apparatus of any example herein, particularly example 19, wherein the convex shape of the distal portion is defined by a hyperbolic curve.

Example 23. The apparatus of any example herein, particularly any one of examples 1-17, wherein the cross-sectional profile of the distal portion has a concave shape relative to a centroid of the distal portion.

Example 24. The apparatus of any example herein, particularly example 23, wherein the concave shape of the distal portion is defined by an elliptical curve.

Example 25. The apparatus of any example herein, particularly example 23, wherein the concave shape of the distal portion is defined by a parabolic curve.

Example 26. The apparatus of any example herein, particularly example 23, wherein the concave shape of the distal portion is defined by a hyperbolic curve.

Example 27. The apparatus of any example herein, particularly any one of examples 1-17, wherein the cross-sectional profile of the distal portion comprises a tip section and a body section proximal to the tip section, wherein the tip section has a concave shape relative to a centroid of the tip section, and the body section has a convex shape relative to a centroid of the body section.

Example 28. The apparatus of any example herein, particularly any one of examples 1-27, wherein the distal portion of the nosecone has an axial length ranging from about 10 mm to about 80 mm.

Example 29. The apparatus of any example herein, particularly example 28, wherein the axial length of the distal portion is about 35 mm.

Example 30. The apparatus of any example herein, particularly any one of examples 28-29, wherein a ratio of an axial length of the proximal portion to the axial length of the distal portion ranges from about 0.03 to about 1.00.

Example 31. The apparatus of any example herein, particularly example 30, wherein the ratio of the axial length of the proximal portion to the axial length of the distal portion is about 0.25.

Example 32. The apparatus of any example herein, particularly any one of examples 1-31, wherein a ratio of an axial length of the nosecone to a maximum diameter of the nosecone ranges from about 1.5 to about 20.0.

Example 33. The apparatus of any example herein, particularly example 32, wherein the ratio of the axial length of the nosecone to the maximum diameter of the nosecone is about 6.5.

Example 34. An apparatus for a transcatheter procedure, the apparatus comprising:

a shaft having a proximal end, a distal end, and a longitudinal axis extending from the proximal end to the distal end; and a nosecone connected to the distal end of the shaft and comprising a distal portion and a proximal portion, wherein the proximal portion of the nosecone comprises a shoulder region adjacent the distal portion of the nosecone, a connection region connected to the distal end of the shaft, and a body region located between the shoulder region and the connection region, wherein an outer surface of the nosecone has a cross-sectional profile taken along the longitudinal axis of the shaft, wherein the cross-sectional profile of the body region comprises a first section having a first slope, a second section having a second slope, and a third section having a third slope, the first section adjacent the connection region, the third section adjacent the shoulder region, and the second section located between the first section and the second section, and wherein the first slope is greater than the second slope and the third slope, the second slope is greater than the third slope.

Example 35. The apparatus of any example herein, particularly example 34, wherein the first slope, the second slope, and the third slope are measured as average slopes in the first section, the second section, and the third section, respectively.

Example 36. The apparatus of any example herein, particularly example 34, wherein the first slope, the second slope, and the third slope are measured as median slopes in the first section, the second section, and the third section, respectively.

Example 37. The apparatus of any example herein, particularly example 34, wherein the first slope, the second slope, and the third slope are measured as maximum slopes in the first section, the second section, and the third section, respectively.

Example 38. The apparatus of any example herein, particularly example 34, wherein the first slope, the second slope, and the third slope are measured as minimum slopes in the first section, the second section, and the third section, respectively.

Example 39. The apparatus of any example herein, particularly any one of examples 34-38, wherein the shaft comprises a lumen extending between the proximal and distal ends of the shaft, wherein the nosecone comprises a lumen extending through the nosecone and linearly connecting to the lumen of the shaft.

Example 40. The apparatus of any example herein, particularly any one of examples 34-39, wherein the distal portion of the nosecone tapers radially outwardly from a distal end of the distal portion to a proximal end of the distal portion, and the proximal portion of the nosecone tapers radially inwardly from the proximal end of the distal portion to a proximal end of the proximal portion, wherein the proximal end of the distal portion has a first diameter, and a distal end of the body region has a second diameter.

Example 41. The apparatus of any example herein, particularly example 40, wherein a difference between the first diameter and the second diameter defines a shoulder depth, wherein the shoulder depth ranges from about 0.1 mm to about 2.5 mm.

Example 42. The apparatus of any example herein, particularly example 41, wherein the shoulder depth is about 1.0 mm.

Example 43. The apparatus of any example herein, particularly any one of examples 41-42, wherein a ratio of the shoulder depth to an axial length of the shoulder region ranges from about 0.02 to about 2.50.

Example 44. The apparatus of any example herein, particularly example 43, wherein the ratio of the shoulder depth to the axial length of the shoulder region is about 0.40.

Example 45. The apparatus of any example herein, particularly any one of examples 40-44, wherein a ratio of the second diameter to the first diameter ranges from about 0.50 to about 0.96.

Example 46. The apparatus of any example herein, particularly example 45, wherein the ratio of the second diameter to the first diameter is about 0.75.

Example 47. The apparatus of any example herein, particularly any one of examples 34-46, wherein a ratio of an axial length of the body region to an axial length of the distal portion ranges from about 0.02 to about 0.95.

Example 48. The apparatus of any example herein, particularly example 47, wherein the ratio of the axial length of the body region to the axial length of the distal portion is about 0.20.

Example 49. The apparatus of any example herein, particularly any one of examples 34-48, wherein the cross-sectional profile of the body region has a convex shape relative to a centroid of the body region.

Example 50. The apparatus of any example herein, particularly example 49, wherein the cross-sectional profile of the body region and the connection region form a continuous convex shape relative to the centroid of the body region.

Example 51. The apparatus of any example herein, particularly any one of examples 34-49, wherein the cross-sectional profile of the connection region has a concave shape relative to a centroid of the connection region.

Example 52. The apparatus of any example herein, particularly any one of examples 34-51, wherein the cross-sectional profile of the shoulder region has a concave shape relative to a centroid of the shoulder region.

Example 53. The apparatus of any example herein, particularly any one of examples 34-52, wherein the shoulder region comprises a peak portion connected to the distal portion of the nosecone and a valley portion connected to the body region, wherein a slope of the shoulder region ranges from about 0 degrees to about 65 degrees.

Example 54. The apparatus of any example herein, particularly example 53, wherein the largest slope in the shoulder region is located at a boundary between the peak portion and the valley portion.

Example 55. The apparatus of any example herein, particularly example 54, wherein the largest slope in the shoulder region ranges from about 15 degrees to about 65 degrees.

Example 56. The apparatus of any example herein, particularly example 55, wherein the largest slope in the shoulder region is about 40 degrees.

Example 57. The apparatus of any example herein, particularly any one of examples 34-56, wherein a slope of the proximal portion varies continuously without a step change.

Example 58. A nosecone for a transcatheter delivery apparatus, the nosecone comprising: a distal portion and a proximal portion; and a longitudinal axis extending from a distal end of the distal portion to a proximal end of the proximal portion, wherein the proximal portion comprises a shoulder region adjacent the distal portion of the nosecone and a body region proximal to the shoulder region, wherein an outer surface of the nosecone has a cross-sectional profile taken along the longitudinal axis of the nosecone, wherein the cross-sectional profile of the body region has a convex shape when viewed from a centroid of the body region.

Example 59. The nosecone of any example herein, particularly example 58, further comprising a lumen extending from the distal end of the distal portion to the proximal end of the proximal portion.

Example 60. The nosecone of any example herein, particularly any one of examples 58-59, wherein the proximal portion further comprises a connection region proximal to the body region, wherein the cross-sectional profile of the connection region has a different curvature than the body region.

Example 61. The nosecone of any example herein, particularly example 60, wherein the cross-sectional profile of the connection region has a concave shape when viewed from a centroid of the connection region.

Example 62. The nosecone of any example herein, particularly any one of examples 60-61, wherein the largest slope of the cross-sectional profile of the connection region ranges from about 20 degrees to about 65 degrees.

Example 63. The nosecone of any example herein, particularly example 62, wherein the largest slope of the cross-sectional profile of the connection region is about 40 degrees.

Example 64. The nosecone of any example herein, particularly any one of examples 58-63, wherein the largest slope of the cross-sectional profile of the shoulder region ranges from about 15 degrees to about 65 degrees.

Example 65. The nosecone of any example herein, particularly example 64, wherein the largest slope of the cross-sectional profile of the shoulder region is about 40 degrees.

Example 66. The nosecone of any example herein, particularly any one of examples 58-65, wherein a proximal end of the distal portion defines a largest diameter of the nosecone.

Example 67. The nosecone of any example herein, particularly any one of examples 58-66, wherein the cross-sectional profile of the body region comprises at least a section, wherein a tangent line at the section does not intercept the cross-sectional profile of the shoulder region.

Example 68. An assembly for a transcatheter procedure, the assembly comprising:
   a shaft having a proximal end, a distal end, and a longitudinal axis extending from the proximal end to the distal end; a nosecone connected to the distal end of the shaft and comprising a distal portion and a proximal portion; and a prosthetic implant releasably connected to a distal end portion of the shaft; wherein the proximal portion of the nosecone comprises a shoulder region adjacent the distal portion of the nosecone, a connection region connected to the distal end of the shaft, and a body region located between the shoulder region and the connection region, wherein an outer surface of the nosecone has a cross-sectional profile taken along the longitudinal axis of the shaft, and wherein the cross-sectional profile of the body region has a convex shape when viewed from a centroid of the body region.

Example 69. The assembly of any example herein, particularly example 68, wherein the prosthetic implant is a prosthetic valve.

Example 70. The assembly of any example herein, particularly example 69, wherein the prosthetic valve comprises a frame having a plurality of struts with a lattice structure.

Example 71. The assembly of any example herein, particularly example 68, wherein the prosthetic implant is a stent.

Example 72. The assembly of any example herein, particularly example 71, wherein the stent comprises a plurality of struts with a lattice structure.

Example 73. The assembly of any example herein, particularly any one of examples 68-72, wherein the prosthetic implant is movable between a radially compressed state and a radially expanded state.

Example 74. The assembly of any example herein, particularly example 73, wherein the prosthetic implant is self-expandable.

Example 75. The assembly of any example herein, particularly example 73, wherein the prosthetic implant is balloon expandable by radially expanding a balloon within the prosthetic implant.

Example 76. The assembly of any example herein, particularly example 73, wherein the prosthetic implant is mechanically expandable by applying an axial force to both a proximal end and a distal end of the prosthetic implant.

Example 77. The assembly of any example herein, particularly any one of examples 68-76, wherein a distal end of the prosthetic implant is disposed adjacent and proximal to the proximal portion of the nosecone.

Example 78. The assembly of any example herein, particularly any one of examples 68-76, wherein a distal end of the prosthetic implant overlaps at least a portion of the proximal portion of the nosecone.

Example 79. The assembly of any example herein, particularly any one of examples 68-78, further comprising a delivery sheath configured to be axially movable relative to the prosthetic implant so that the prosthetic implant is covered by the delivery sheath when a distal end of the delivery sheath abuts the shoulder region of the nosecone and the prosthetic implant can be exposed when the delivery sheath is moved proximal relative to the prosthetic implant.

Example 80. The assembly of any example herein, particularly example 79, wherein a distal end of the shoulder region defines a largest diameter of the nosecone, and wherein the distal end of the delivery sheath and the distal end of the shoulder region have about the same diameter.

Example 81. The assembly of any example herein, particularly any one of examples 79-80, wherein the shaft is an inner shaft, and the assembly further comprises an outer shaft extending over the inner shaft.

Example 82. The assembly of any example herein, particularly example 81, wherein a distal end of the outer shaft connects to a proximal end of the delivery sheath.

Example 83. The assembly of any example herein, particularly example 81, wherein the delivery sheath is an integral part of the outer shaft.

Example 84. The assembly of any example herein, particularly any one of examples 81-83, wherein a proximal end of the inner shaft and a proximal end of the outer shaft are connected to a handle, wherein the handle comprises a drive mechanism configured to effectuate axial movement of the outer shaft relative to the inner shaft.

Example 85. The assembly of any example herein, particularly example 84, wherein the handle comprises an adjustment mechanism configured to adjust curvature of the outer shaft.

Example 86. The assembly of any example herein, particularly any one of examples 81-85, further comprising an intermediate shaft extending between the inner shaft and the outer shaft, wherein a distal end of the intermediate shaft is connected to a balloon disposed within the prosthetic implant, and wherein a proximal end of the intermediate shaft is connected to an inflation mechanism configured to radially expand the balloon.

Example 87. The assembly of any example herein, particularly any one of examples 68-86, wherein the cross-sectional profile of the body region comprises at least a section, wherein a tangent line at the section does not intercept the cross-sectional profile of the shoulder region.

Example 88. The assembly of any example herein, particularly example 87, wherein the section extends from a proximal end of the body region to a mid-point of the body region.

In view of the many possible embodiments to which the principles of the disclosure may be applied, it should be recognized that the illustrated embodiments are only examples and should not be taken as limiting the scope of the disclosure or the claims. Rather, the scope of the claimed subject matter is defined by the following claims and their equivalents.

The invention claimed is:

1. An apparatus for a transcatheter procedure, the apparatus comprising:
   a shaft having a proximal end, a distal end, and a longitudinal axis extending from the proximal end to the distal end; and
   a nosecone connected to the distal end of the shaft and comprising a distal portion and a proximal portion,
   wherein the proximal portion of the nosecone comprises a shoulder region adjacent the distal portion of the nosecone, a connection region connected to the distal end of the shaft, and a body region located between the shoulder region and the connection region,
   wherein an outer surface of the nosecone has a cross-sectional profile taken along the longitudinal axis of the shaft,
   wherein the cross-sectional profile of the body region comprises a first section having a first slope, a second section having a second slope, and a third section having a third slope, the first section adjacent the connection region, the third section adjacent the shoulder region, and the second section located between the first section and the second section, and
   wherein the first slope is greater than the second slope and the third slope, the second slope is greater than the third slope,
   wherein the shoulder region has a shoulder depth defined as one-half of a difference between a maximum outer diameter of the shoulder region and a minimum outer diameter of the shoulder region, and wherein a ratio of the shoulder depth to an axial length of the shoulder region ranges from about 0.02 to about 2.50.

2. The apparatus of claim 1, wherein the distal portion of the nosecone tapers radially outwardly from a distal end of the distal portion to a proximal end of the distal portion, and the proximal portion of the nosecone tapers radially inwardly from the proximal end of the distal portion to a proximal end of the proximal portion, wherein the proximal end of the distal portion has a first diameter, and a distal end of the body region has a second diameter.

3. The apparatus of claim 1, wherein the shoulder depth ranges from about 0.1 mm to about 2.5 mm.

4. The apparatus of claim 2, wherein a ratio of the second diameter to the first diameter ranges from about 0.50 to about 0.96.

5. The apparatus of claim 1, wherein a ratio of an axial length of the body region to an axial length of the distal portion ranges from about 0.02 to about 0.95.

6. The apparatus of claim 1, wherein the cross-sectional profile of the body region has a convex shape relative to a centroid of the body region.

7. The apparatus of claim 1, wherein the cross-sectional profile of the shoulder region has a concave shape relative to a centroid of the shoulder region.

8. The apparatus of claim 1, wherein the shoulder region comprises a peak portion connected to the distal portion of the nosecone and a valley portion connected to the body region, wherein a slope of the shoulder region ranges from about 0 degrees to about 65 degrees.

9. The apparatus of claim 1, wherein a slope of the proximal portion varies continuously without a step change.

* * * * *